(12) United States Patent
Pericle et al.

(10) Patent No.: US 9,371,265 B2
(45) Date of Patent: Jun. 21, 2016

(54) COMPOSITIONS AND METHODS RELATED TO INHIBITORS OF JAK KINASE

(71) Applicant: EP PHARMA, INC., El Paso, TX (US)

(72) Inventors: Federica Pericle, El Paso, TX (US); Jeremy A. Ross, El Paso, TX (US)

(*) Notice: Subject to any disclaimer, the term of this patent is extended or adjusted under 35 U.S.C. 154(b) by 0 days.

(21) Appl. No.: 14/387,890

(22) PCT Filed: Mar. 26, 2013

(86) PCT No.: PCT/US2013/033819
§ 371 (c)(1),
(2) Date: Sep. 25, 2014

(87) PCT Pub. No.: WO2013/148638
PCT Pub. Date: Oct. 3, 2013

(65) Prior Publication Data
US 2015/0087621 A1    Mar. 26, 2015

Related U.S. Application Data

(60) Provisional application No. 61/615,372, filed on Mar. 26, 2012.

(51) Int. Cl.
C07C 59/82    (2006.01)
C07F 9/09     (2006.01)
A61K 31/6615  (2006.01)

(52) U.S. Cl.
CPC ............ *C07C 59/82* (2013.01); *A61K 31/6615* (2013.01); *C07F 9/09* (2013.01); *C07C 2101/20* (2013.01)

(58) Field of Classification Search
CPC ........ C07C 59/82; C07F 9/09; A61K 31/6615
See application file for complete search history.

(56) References Cited

U.S. PATENT DOCUMENTS 7,365,096 B2 * 4/2008 Kirken ................. A61K 31/335
                                                424/49

OTHER PUBLICATIONS

Thoma et al. "Selective inhibitors of the Janus kinase Jak3—Are they effective?" Bioorganic & Medicinal Chemistry Letters, 2014, vol. 24, p. 4617-4621.*
Patani et al. "Bioisosterism: A Rational Approach in Drug Design" Chemical Reviews, 1996, vol. 96, pp. 3147-3176.*

* cited by examiner

*Primary Examiner* — Joseph Kosack
(74) *Attorney, Agent, or Firm* — Norton Rose Fulbright US LLP

(57) ABSTRACT

Embodiments are directed to JAK kinase inhibiting prodrug compounds of Formula Ib, containing a promoiety that results in alcohol derivative of the parent compound upon removal and methods of using an effective amount of said prodrug compounds in the treatment of a JAK-mediated disease or disorder in a subject. Preferred promoieties include phosphate, phosphonate, phosphate salt, sulfate, or sulfate salt.

6 Claims, 11 Drawing Sheets

A
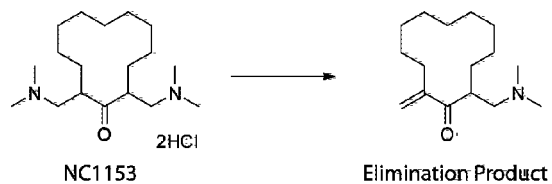
B
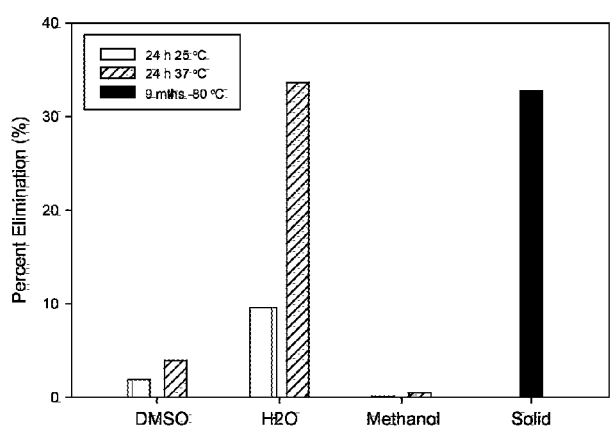
FIGs. 10A-10B
A
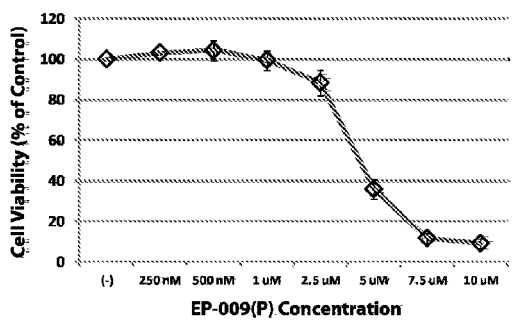
B
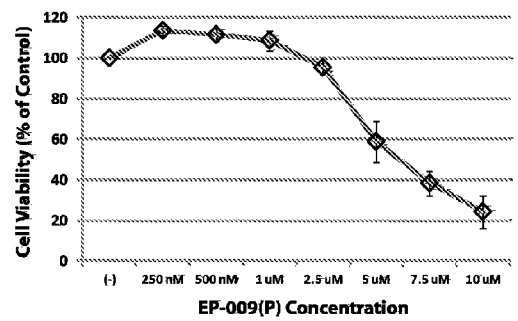
FIGs. 11A-11B

COMPOSITIONS AND METHODS RELATED TO INHIBITORS OF JAK KINASE

PRIORITY PARAGRAPH

This application is a U.S. National Stage Application of International Application serial number PCT/US2013/033819 filed Mar. 26, 2013, which claims priority to U.S. Provisional Application Ser. No. 61/615,372 filed Mar. 26, 2012. This application claims priority to and incorporates by reference each of the above referenced applications in their entirety.

STATEMENT REGARDING FEDERALLY FUNDED RESEARCH

This invention was made with government support under 1R43RR032354-01 awarded by the National Institutes of Health. The government has certain rights in the invention.

BACKGROUND

Embodiments of the invention are directed generally to the field of medicine. Certain embodiments are directed to the field of oncology and cancer therapeutics.

Recent therapeutic strategies to combat immune-derived diseases have focused on T-cell signaling pathways and the molecules that comprise them. T-cell signaling cascades and their potential role as molecular targets for the treatment of immunoflammatory disease like rheumatoid arthritis, inflammatory bowel disease, psoriasis, and for the prevention of transplant rejection are described in "*Drugs RD*, 2010; 10(4)" comprehensive review.

Complete activation of T-cells requires three threshold-limited sequential signals. A first signal delivered by antigens that engage a specific T-cell receptor (TCR) is followed by a second signal delivered by a B7/CD28 interaction. Within seconds to minutes after TCR engagement, the CD3ζ chain is tyrosine (Tyr) phosphorylated during the autoactivation of Zap70, Lck, and Fyn protein Tyr kinases. Concomitantly, calcium (Ca2+) mobilization triggers catalytic activation of CaN phosphatase to dephosphorylate nuclear factor of activated T-cell (NFAT)—a necessary step for NFAT to translocate to the nucleus and bind discrete DNA binding elements within the promoter of the interleukin (IL)-2 gene. The first and second signals are critical for the synthesis and secretion of IL-2, which, in concert with other T-cell growth factors (TCGFs) such as IL-4, -7, -9, -13, -15 and -21, deliver a third signal through cytokine receptors, a necessary step required to drive clonal expansion of T-cells. These cytokine receptors share a common γ chain ($\gamma_e$) that when combined with a unique α-chain for each cytokine deliver intracellular signals via Janus tyrosine kinase (JAK) JAK1 and JAK3, as well as activate signal transducers and activators of transcription (Stat) Stat1, Stat3, Stat5a/b and Stat6.

Unlike other signaling pathway molecules that serve as candidate targets for therapeutic intervention, JAK3 expression shows a limited pattern of tissue expression and is compartmentalized to T-cells, B-cells, natural killer (NK) cells and monocytes, or in general terms to cells of immune origin. Because of the involvement of JAK3 in T-cell activation and proliferation, and the documented genetic evidence for the role of JAK3 in autoimmune or transplant-induced inflammatory disorders, the selective targeting of JAK3 in T-cells may potentially be clinically beneficial in T-cell-derived pathologic disorders. Recently, JAK3 activation has been reported in several lymphoid malignancies, including cutaneous T-cell lymphoma, anaplastic large cell lymphoma mantle-cell lymphoma, HTLV-1-induced adult T-cell leukemia, Burkitt lymphoma, and acute lymphoblastic leukemia. Thus, JAK3 is a viable molecular target in the treatment of immune-mediated diseases and a broad range of hematopoietic cancers. These malignancies represent an aggressive subset of blood cancers and despite advancement in the treatment of these cancers, patients who do not respond to standard therapy or relapse face a very poor prognosis. Thus, there is a need for additional therapies and compounds to address these unmet medical needs.

SUMMARY

Embodiments of the invention are directed to compounds that inhibit JAK kinase, e.g., JAK3, and prodrugs thereof. Certain embodiments are directed to a prodrug of a JAK kinase, e.g., JAK3, inhibitor. As used herein, a prodrug is a modified compound (drug) administered in an inactive or less active form. Once administered, the prodrug is metabolized or chemically transformed in vivo into an active or more active compound. The rationale behind the use of a prodrug is generally for absorption, distribution, metabolism, and excretion (ADME) optimization. Prodrugs can be classified into two major types, based on their cellular sites of activation into active drug form, with Type I being those that are activated intracellularly, and Type II being those that are activated extracellularly, especially in digestive fluids or the systemic circulation.

Certain embodiments are directed to compound having a general formula of Formula Ia or Formula Ib. In certain aspect the compound has a formula of Formula Ia:

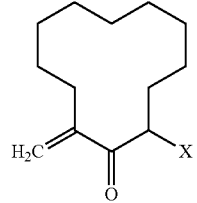

Formula Ia where X is C1-C4 alkanol. In certain aspects X is —COH.

In other aspects, the compound has the general formula of Formula Ib:

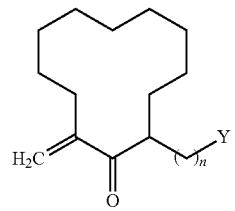

Formula Ib where n is 0, 1, 2, 3, 4, 5, or 6; and Y is a promoiety. In a further aspect, n is 1, 2, or 3. Y represents a hydrolyzable promoiety, thus the promoiety can be removed in vivo to activate (bio-activation) the compound of Formula Ib.

A "promoiety" is a chemically or metabolically labile moiety that alters the physical properties of the compound of Formula Ia. In certain aspects, the promoiety can be an ester or carbonate ester of an organic acid (e.g., succinate, acetate or fumarate), an amino acid (e.g., glycinate), a polyhydric alcohol (e.g., polyethylene glycol or ethylene glycol) or a polyether. In certain embodiments the promoiety is hydrolyzed to form an alcohol of Formula Ia. In certain aspects, the promoiety is methyl, ethyl, isopropyl, n-propyl, tert-butyl, butyl, pentyl, methoxy, tert-butoxy, methoxyethyl, ethoxymethyl, methoxy-methyl, phenyl, carboxyethyl, methoxycarbonylmethyl, methoxycarbonylethyl, tert-butoxycarbonylaminomethyl, methoxycarbonyl, aminomethyl, and methylcarbonyl-aminomethyl; or a pharmaceutically acceptable salt thereof. In a further aspect, the promoiety is a fatty acid such as, but not limited to arachidic, stearic, palmitic, myristoleic, palmitoleic, oleic acid, linoleic acid and the like. In certain aspects, the promoiety is phosphate, phosphate salt, phosphoester, and the like. In still a further aspect, the promoiety is sulfate, sulfate salt, or the like.

Certain embodiments are directed to phosphoester prodrugs of Formula Ia having a general formula of Formula IIa or Formula IIb:

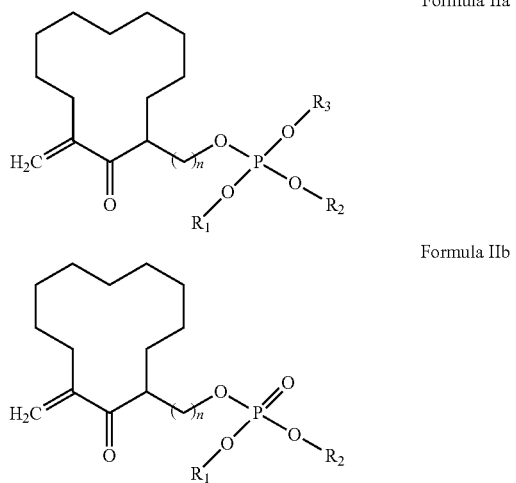

Formula IIa

Formula IIb where n is as defined above and $R_1$, $R_2$, and $R_3$ are each independently hydrogen, C1-C5 alkyl, substituted or unsubstituted cycloalkyl, substituted or unsubstituted heteroalkyl, substituted or unsubstituted aryl, a substituted or unsubstituted heteroaryl.

Certain embodiments are directed to use of the compounds described above for the treatment of disease and conditions related to JAK3 kinase activity, such as cancer, immunological, inflammatory, metabolic, infectious, and vascular diseases.

Human hematopoietic tumors expressing hyper-activated JAK3 may be susceptible to anti-tumor agents that inhibit the activity of JAK3 in cancer cells. Limited progress has been reported in hematopoietic diseases such as lymphoma/leukemia. The methods described herein are generally useful for treatment of various diseases, including cancers, especially hematopoietic cancers (such as acute myeloid leukemia). A "hematopoietic cancer" is a neoplasm or cancer of hematopoietic cells of the blood or lymph system and includes disease states such as Hodgkin's disease, non-Hodgkin's lymphoma, including anaplastic large-cell lymphoma, cutaneous T-cell lymphoma, adult T-cell lymphoma, peripheral T-cell lymphoma, leukemias, including non-acute and acute leukemias, such as acute myelogenous leukemia, acute lymphocytic leukemia, acute promyelocytic leukemia (APL), adult T-cell leukemia, T-lineage acute lymphoblastic leukemia (T-ALL), basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia and stem cell leukemia, among others.

As used herein, "treatment" is an approach for obtaining beneficial or desired clinical results. Beneficial or desired clinical results include, but are not limited to, any one or more of: alleviation of one or more symptoms, diminishment of extent of disease, stabilized (i.e., not worsening) state of disease, preventing or delaying spread (e.g., metastasis) of disease, preventing or delaying occurrence or recurrence of disease, delay or slowing of disease progression, amelioration of the disease state, and remission (whether partial or total). Also encompassed by "treatment" is a reduction of pathological consequence of a disease. The methods of the invention contemplate any one or more of these aspects of treatment.

The term "effective amount" used herein refers to an amount of a compound or composition sufficient to treat a specified disorder, condition, or disease such as ameliorate, palliate, lessen, and/or delay one or more of its symptoms. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some variations, an effective amount is an amount sufficient to prevent or delay occurrence and/or recurrence. An effective amount can be administered in one or more administrations. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

The term "individual", "subject", or "patient" is a mammal, including humans. Individuals or patients include, but are not limited to, humans, bovines, horses, cats, dogs, rodents, or primates.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIGS. 10A-10B illustrates stability analysis of the NC1153 dihydrochloride salt (A) using NMR and HPLC indicates the compound decomposes from cleavage of a single dimethylamino group (Elimination Product). (B) Although soluble in water, NC1153 decomposes at an observed rate of 10% and 33% in 24 hr at 25° C. and 37° C., respectively (A and B).

FIGS. 11A-11B illustrates the dose-dependent effect of (A) freshly prepared EP-009(P) and (B) EP-009(P) stored in aqueous conditions for 48 hr at room temperature on IL-2/JAK3-dependent Kit225 cell viability.

DESCRIPTION

Figures 1A, 1B, 1C, 1D:
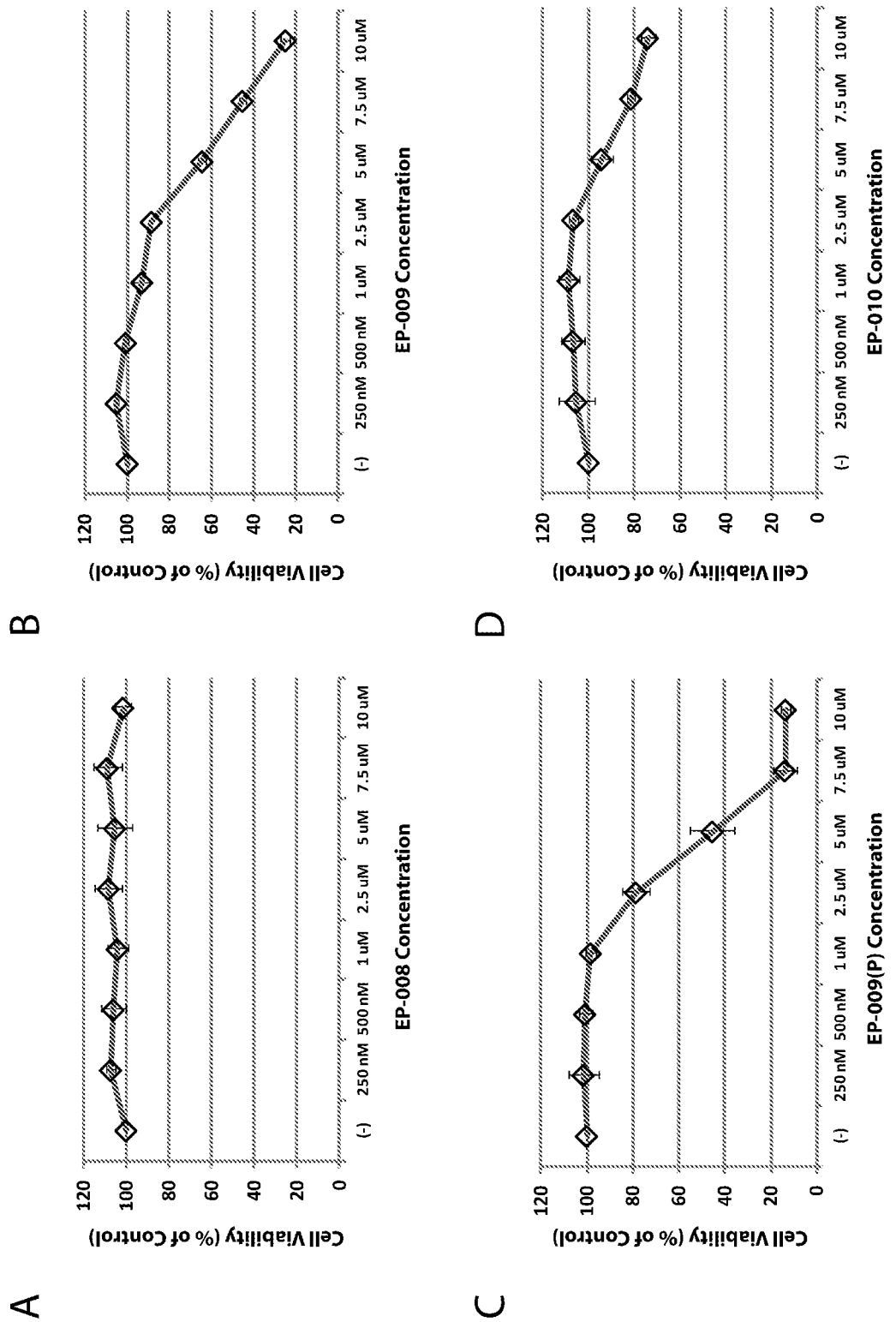
FIGS. 1A-1D. Dose-dependent effect of (A) EP-008, (B) EP-009, (C) EP-009(P) and (D) EP-010 on IL-2/JAK3-dependent Kit225 cell viability. Kit225 cells were seeded in 96-well plates (3 wells/treatment) and treated with DMSO (0.1%) or ascending amounts of EP compound as indicated. MTS reagent was added and OD 490-650 nm determined at 72 h. Data represent mean OD normalized to DMSO treated control, while error bars represent the standard deviation (FIGS. 1A-1D).

Proliferation and differentiation of hematopoietic cells is dependent upon the binding of hematopoietic growth factors and cytokines to their respective cell surface receptors (Cross et al., *Cell,* 64:271, 1991; Ogawa, *Blood,* 81:2844, 1993; Heimfeld et al., *Proc. Natl. Acad. Sci. USA,* 88:9902, 1991). Some of these receptors transduce the signal at the cell surface to the cytoplasm through the activation of a tyrosine kinase domain in the cytoplasmic portion of the receptor (e.g., CSF1, c-kit, STK-1/FLT3/FLK2-) (Boyle, Current Opinion in Oncology, 4:156, 1992, Chiba et al, *Nature,* 362:646, 1993, Schlessinger et al., *Neuron,* 9:383, 1992, Ullrich and Schlessinger, *Cell,* 61:203, 1990). Another group of hematopoietic receptors lack intrinsic kinase catalytic domains (e.g., IL-3, GM-CSF, G-CSF, and EPO receptors) (Miyajima et al., *Blood,* 82:1960, 1993; Fukunaga et al., *EMBO,* 10:2855, 1991; Wojchowski et al., *Stem Cells,* 11:381, 1993), however, upon binding of their ligands, these receptors activate protein tyrosine phosphorylation of second messengers and the subsequent signal pathways to the cell's nucleus (Kishimoto et al., *Science,* 258:593, 1992; Stahl et al., *Cell,* 74:587, 1993).

Tyrosine kinases often play pivotal roles in the proliferation and differentiation of many cell types. Many growth factor receptors contain a tyrosine kinase domain as part of their cytoplasmic tail such that binding by ligand directly activates their tyrosine kinase activity. However, many other receptors do not contain a tyrosine kinase domain in their cytoplasmic tail. Addition of ligand to many cell types expressing these receptors still results in increased levels of phosphotyrosine. The Janus kinase (JAK) family, a series of related intracellular tyrosine kinases, has been shown to link these receptors and other members of the signal transduction pathway.

One member of the JAK family is the tyrosine-protein kinase JAK3. JAK3 functions in signal transduction and interacts with members of the STAT (signal transduction and activators of transcription) family. JAK3 is predominantly expressed in immune cells and transduces a signal in response to its activation via tyrosine phosphorylation by interleukin receptors.

JAK3 gene expression is restricted mostly to hematopoietic cells and its role in cytokine signaling is thought to be more restricted than other JAKs. It is most commonly expressed in T-cells and NK cells, but has been induced in other leukocytes, including monocytes. JAK3 is involved in signal transduction by receptors that employ the common gamma chain ($\gamma_c$) of the type I cytokine receptor family (e.g. IL-2R, IL-4R, IL-7R, IL-9R, IL-15R, and IL-21R).

I. DISEASES AND CONDITIONS RELATED TO JAK3 KINASE ACTIVITY

JAK3 is a viable molecular target in the treatment of a broad range of hematopoietic cancers and T/B cell-derived disease (e.g. RA, inflammatory bowel disease, dry eyes, ankylosing spondylitis, psoriasis, viral, metabolic, etc.). The inventors have developed therapeutic compounds for the treatment of diseases that display Janus tyrosine kinase (JAK3) dysregulation.

JAK3 activation has been reported in several lymphoid malignancies, including cutaneous T-cell lymphoma, anaplastic large cell lymphoma mantle-cell lymphoma, HTLV-1-induced adult T-cell leukemia, Burkitt lymphoma and acute lymphoblastic leukemia. These malignancies represent an aggressive subset of blood cancers and despite advancement in the treatment of these cancers, patients who do not respond to standard therapy or relapse face a very poor prognosis. Thus there is a significant need for novel therapies to address these unmet medical needs.

The present invention provides pharmaceutical compositions comprising a compound of formula Ia, Ib, IIa, or IIb, or a pharmaceutically acceptable salt thereof as active ingredient together with a pharmaceutically acceptable carrier, optionally in combination with one or more other pharmaceutical compositions.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The term "carrier" refers to a diluent, adjuvant, excipient, or vehicle (e.g., liposome) with which the therapeutic is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water can be used as a carrier when the pharmaceutical composition is administered orally. Saline and aqueous dextrose can be used as carriers when the pharmaceutical composition is administered intravenously. Saline solutions and aqueous dextrose and glycerol solutions are typically employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the patient. The formulation should suit the mode of administration.

The compounds of the present invention or pharmaceutically acceptable salt(s) thereof and the other pharmaceutically active agent(s) may be administered together or separately and, when administered separately, this may occur separately or sequentially in any order. When combined in the same formulation it will be appreciated that the two compounds must be stable and compatible with each other and the other components of the formulation. When formulated separately they may be provided in any convenient formulation, conveniently in such manner as are known for such compounds in the art.

It is further included within the present invention that the compounds described herein, or a pharmaceutically acceptable salt thereof, or a pharmaceutical composition comprising a compound described herein is administered in combination with another drug or pharmaceutically active agent and/or that the pharmaceutical composition of the invention further comprises such a drug or pharmaceutically active agent.

In this context, the term "drug or pharmaceutically active agent" includes a drug or pharmaceutical agent that will elicit the biological or medical response of a tissue, system, animal or human that is being sought, for instance, by a researcher or clinician.

"Combined" or "in combination" or "combination" should be understood as a functional coadministration, wherein some or all compounds may be administered separately, in different formulations, different modes of administration (for example subcutaneous, intravenous or oral) and different times of administration. The individual compounds of such combinations may be administered either sequentially in separate pharmaceutical compositions as well as simultaneously in combined pharmaceutical compositions.

For example, in rheumatoid arthritis therapy, combination with other chemotherapeutic or antibody agents is envisaged. Suitable examples of pharmaceutically active agents which may be employed in combination with the compounds of the present invention and their salts for rheumatoid arthritis therapy include: immunosuppresants such as amtolmetin guacil, mizoribine and rimexolone; anti-TNFα agents such as etanercept, infliximab, Adalimumab, Anakinra, Abatacept, Rituximab; tyrosine kinase inhibitors such as leflunomide; kallikrein antagonists such as subreum; interleukin 11 agonists such as oprelvekin; interferon beta 1 agonists; hyaluronic acid agonists such as NRD-101 (Aventis); interleukin 1 receptor antagonists such as anakinra; CD8 antagonists such as amiprilose hydrochloride; beta amyloid precursor protein antagonists such as reumacon; matrix metalloprotease inhibitors such as cipemastat and other disease modifying anti-rheumatic drugs (DMARDs) such as methotrexate, sulphasalazine, cyclosporin A, hydroxychoroquine, auranofin, aurothioglucose, gold sodium thiomalate and penicillamine.

In particular, the treatment defined herein may be applied as a sole therapy or may involve, in addition to the compounds of the invention, conventional surgery or radiotherapy or chemotherapy. Accordingly, the compounds of the invention can also be used in combination with existing therapeutic agents for the treatment proliferative diseases such as cancer. Suitable agents to be used in combination include:

(i) antiproliferative/antineoplastic drugs and combinations thereof, as used in medical oncology such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea and gemcitabine); antitumor antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like paclitaxel and taxotere); and topoisomerase inhibitors (for example epipodophyllotoxins like etoposide and teniposide, amsacrine, topotecan and camptothecins);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxy-quinazoline (AZD0530) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825), and metalloproteinase inhibitors like marimastat and inhibitors of urokinase plasminogen activator receptor function);

(iv) inhibitors of growth factor function: for example such inhibitors include growth factor antibodies and growth factor receptor antibodies (for example the anti-erbB2 antibody trastuzumab [Herceptin™] and the anti-erbB1 antibody cetuximab [C225]); such inhibitors also include, for example, tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD 1839), Ν-(3-ethynylphenyl)-6,7-bis(2- methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033) and erbB2 tyrosine kinase inhibitors such as lapatinib), inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)) and inhibitors of cell signalling through MEK and/or Akt kinases;

(v) antiangiogenic agents such as those which inhibit the effects of vascular endothelial growth factor, for example the anti-vascular endothelial cell growth factor antibody bevacizumab (Avastin™) and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy) quinazoline (AZD2171; Example 240 within WO 00/47212), vatalanib (PTK787; WO 98/35985) and SUI 1248 (sunitinib; WO 01/60814), and compounds that work by other mechanisms (for example linomide, inhibitors of integrin αvβ3 function and angiostatin);

(vi) vascular damaging agents such as combretastatin A4 and compounds disclosed in International Patent Application WO 99/02166;

(vii) antisense therapies, for example those which are directed to the targets listed above, such as ISIS 2503, an anti-Ras antisense agent;

(viii) gene therapy approaches, including approaches to replace aberrant genes such as aberrant p53 or aberrant BRCA1 or BRCA2, GDEPT (gene-directed enzyme prodrug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapeutic approaches, including ex-vivo and in-vivo approaches to increase the immunogenicity of patient tumor cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumor cell lines and approaches using anti-idiotypic antibodies.

Accordingly, the individual compounds of such combinations may be administered either sequentially in separate pharmaceutical compositions as well as simultaneously in combined pharmaceutical compositions.

The pharmaceutical compositions of the present invention include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds described herein can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally, for example, as liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds described herein may also be administered parenterally. Solutions or suspensions of these active compounds can be prepared in water suitably mixed with a surfactant such as hydroxypropyl-cellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In certain cases, the form must be sterile and must be fluid to the extent that easy syringability exists. It can be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of formula (I) are administered orally.

The effective dosage of active ingredient employed may vary depending on the particular compound employed, the mode of administration, the condition being treated and the severity of the condition being treated. Such dosage may be ascertained readily by a person skilled in the art.

A therapeutically effective amount of a compound of the present invention will normally depend upon a number of factors including, for example, the age and weight of the animal, the precise condition requiring treatment and its severity, the nature of the formulation, and the route of administration. However, an effective amount of a compound described herein for the treatment of an inflammatory disease, for example rheumatoid arthritis (RA), will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a pharmaceutically acceptable salt, prodrug or metabolite thereof, may be determined as a proportion of the effective amount of the compounds described herein. It is envisaged that similar dosages would be appropriate for treatment of the other conditions referred to above.

As used herein, the term "effective amount" means that amount of a drug or pharmaceutical agent that will elicit the biological or medical response of a tissue, system, animal or human that is being sought, for instance, by a researcher or clinician.

Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Another aspect of the present invention is a compound of the present invention or a pharmaceutically acceptable salt thereof for use as a medicament.

Another aspect of the present invention is a compound of the present invention or a pharmaceutically acceptable salt thereof for use in a method of treating or preventing a disease or disorder associated with JAK3. In the context of the present invention, a disease or disorder associated with JAK3 is defined as a disease or disorder where JAK3 is involved.

In a preferred embodiment, wherein the diseases or disorder is associated with JAK3 is an immunological, inflammatory, autoimmune, or allergic disorder or disease of a transplant rejection or a Graft-versus host disease.

Consequently, another aspect of the present invention is a compound or a pharmaceutically acceptable salt thereof of the present invention for use in a method of treating or preventing an immunological, inflammatory, autoimmune, or allergic disorder or disease of a transplant rejection or a Graft-versus host disease.

Inflammation of tissues and organs occurs in a wide range of disorders and diseases and in certain variations, results from activation of the cytokine family of receptors. Examples of inflammatory disorders associated with activation of JAK3 include, in a non-limiting manner, skin inflammation due radiation exposure, asthma, allergic inflammation and chronic inflammation.

According to the present invention, an autoimmune disease is a disease that is at least partially provoked by an immune reaction of the body against own components, for example proteins, lipids or DNA. Examples of organ-specific autoimmune disorders are insulin-dependent diabetes (Type I) which affects the pancreas, Hashimoto's thyroiditis and Graves' disease which affect the thyroid gland, pernicious anemia which affects the stomach, Cushing's disease and Addison's disease which affect the adrenal glands, chronic active hepatitis which affects the liver; polycystic ovary syndrome (PCOS), celiac disease, psoriasis, inflammatory bowel disease (IBD) and ankylosing spondylitis. Examples of non-organ-specific autoimmune disorders are rheumatoid arthritis, multiple sclerosis, systemic lupus and myasthenia gravis.

Type I diabetes ensues from the selective aggression of autoreactive T-cells against insulin secreting beta-cells of the islets of Langerhans. Targeting JAK3 in this disease is based on the observation that multiple cytokines that signal through the JAK pathway are known to participate in the T-cell mediated autoimmune destruction of beta-cells. Indeed, a JAK3 inhibitor, JANEX-1 was shown to prevent spontaneous autoimmune diabetes development in the NOD mouse model of type I diabetes.

In a preferred embodiment, the autoimmune disease is selected from the group consisting of rheumatoid arthritis (RA), inflammatory bowel disease (IBD; Crohns's disease and ulcerative colitis), psoriasis, systemic lupus erythematosus (SLE), and multiple sclerosis (MS).

Rheumatoid arthritis (RA) is a chronic progressive, debilitating inflammatory disease that affects approximately 1% of the world's population. RA is a symmetric polyarticular arthritis that primarily affects the small joints of the hands and feet. In addition to inflammation in the synovium, the joint lining, the aggressive front of tissue called pannus invades and destroys local articular structures (Firestein, *Nature* 423: 356-361, 2003).

Inflammatory bowel disease (IBD) is characterized by a chronic relapsing intestinal inflammation. IBD is subdivided into Crohn's disease and ulcerative colitis phenotypes. Crohn disease involves most frequently the terminal ileum and colon, is transmural and discontinuous. In contrast, in ulcerative colitis, the inflammation is continuous and limited to rectal and colonic mucosal layers. In approximately 10% of cases confined to the rectum and colon, definitive classification of Crohn disease or ulcerative colitis cannot be made and are designated 'indeterminate colitis.' Both diseases include extraintestinal inflammation of the skin, eyes, or joints. Neutrophil-induced injuries may be prevented by the use of neutrophils migration inhibitors (Asakura et al., *World J Gastroenterol.* 13(15):2145-9, 2007).

Psoriasis is a chronic inflammatory dermatosis that affects approximately 2% of the population. It is characterized by red, scaly skin patches that are usually found on the scalp, elbows, and knees, and may be associated with severe arthritis. The lesions are caused by abnormal keratinocyte proliferation and infiltration of inflammatory cells into the dermis and epidermis (Schon et al., *New Engl. J. Med.* 352:1899-1912, 2005).

Systemic lupus erythematosus (SLE) is a chronic inflammatory disease generated by T-cell-mediated B-cell activation, which results in glomerulonephritis and renal failure. Human SLE is characterized at early stages by the expansion of long-lasting autoreactive CD4+ memory cells (D'Cruz et al., *Lancet* 369(9561):587-96, 2007).

Multiple sclerosis (MS) is an inflammatory and demyelating neurological disease. It has bee considered as an autoimmune disorder mediated by CD4+ type 1 T helper cells, but recent studies indicated a role of other immune cells (Hemmer et al., *Nat. Rev. Neuroscience* 3, 291-301, 2002).

Mast cells express JAK3 and JAK3 is a key regulator of the IgE mediated mast cell responses including the release of inflammatory mediators. JAK3 was shown to be a valid target in the treatment of mast cell mediated allergic reaction. Allergic disorders associated with mast cell activation include Type I immediate hypersensitivity reactions such as allergic rhinitis (hay fever), allergic urticaria (hives), angioedema, allergic asthma and anaphylaxis, for example anaphylatic shock. These disorders may be treated or prevented by inhibition of JAK3 activity, for example, by administration of a JAK3 inhibitor according to the present invention.

Transplant rejection (allograft transplant rejection) includes, without limitation, acute and chronic allograft rejection following for example transplantation of kidney, heart, liver, lung, bone marrow, skin and cornea. It is known that T-cells play a central role in the specific immune response of allograft rejection. Hyperacute, acute and chronic organ transplant rejection may be treated. Hyperacute rejection occurs within minutes of transplantation. Acute rejection generally occurs within six to twelve months of the transplant. Hyperacute and acute rejections are typically reversible where treated with immunosuppressant agents. Chronic rejection, characterized by gradual loss of organ function, is an ongoing concern for transplant recipients because it can occur anytime after transplantation.

Graft-versus-host disease (GVDH) is a major complication in allogeneic bone marrow transplantation (BMT). GVDH is caused by donor T-cells that recognize and react to recipient differences in the histocompatibility complex system, resulting in significant morbidity and mortality. JAK3 plays a key role in the induction of GVHD and treatment with a JAK3 inhibitor, JANEX-1, was shown to attenuate the severity of GVHD.

In a further preferred embodiment, the disease or disorder associated with JAK3 is a proliferative disease, especially cancer.

Diseases and disorders associated especially with JAK3 are proliferative disorders or diseases, especially cancer.

Therefore, another aspect of the present invention is a compound or a pharmaceutically acceptable salt thereof of the present invention for use in a method of treating or preventing a proliferative disease, especially cancer.

Cancer comprises a group of diseases characterized by uncontrolled growth and spread of abnormal cells. All types of cancers generally involve some abnormality in the control of cell growth, division and survival, resulting in the malignant growth of cells. Key factors contributing to said malignant growth of cells are independence from growth signals, insensitivity to anti-growth signals, evasion of apoptosis, limitless replicative potential, sustained angiogenesis, tissue invasion and metastasis, and genome instability (Hanahan and Weinberg, *Cell* 100, 57-70, 2000).

Typically, cancers are classified as hematological cancers (for example leukemias and lymphomas) and solid cancers such as sarcomas and carcinomas (for example cancers of the brain, breast, lung, colon, stomach, liver, pancreas, prostate, ovary).

The JAK3 inhibitors of the present invention may also useful in treating certain malignancies, including skin cancer and hematological malignancy such as lymphomas and leukemias.

Especially cancers in which the JAK-STAT signal transduction pathway is activated, for example due to activation of JAK3 are expected to respond to treatment with JAK3 inhibitors. Examples of cancers harboring JAK3 mutations are acute megakaryoblastic leukemia (AMKL) (Walters et al., *Cancer Cell* 10(1):65-75, 2006) and breast cancer (Jeong et al., *Clin. Cancer Res.* 14, 3716-21, 2008).

Proliferative diseases or disorders comprise a group of diseases characterized by increased cell multiplication as observed in myeloprolifetative disorders (MPD) such as polycythemia vera (PV).

Yet another aspect of the present invention is the use of a compound of the present invention or a pharmaceutically acceptable salt thereof for the manufacture of a medicament for the treatment or prophylaxis of diseases and disorders associated with JAK3.

Yet another aspect of the present invention is the use of a compound of the present invention or a pharmaceutically acceptable salt thereof for the manufacture of a medicament for treating or preventing an immunological, inflammatory, autoimmune, or allergic disorder or disease or a transplant rejection or a Graft-versus host disease.

Yet another aspect of the present invention is the use of a compound of the present invention or a pharmaceutically acceptable salt thereof for the manufacture of a medicament for treating or preventing a proliferative disease, especially cancer.

In the context of these uses of the invention, diseases and disorders associated with JAK3 are as defined above.

Yet another aspect of the present invention is a method for treating, controlling, delaying or preventing in a mammalian patient in need thereof one or more conditions selected from the group consisting of diseases and disorders associated with JAK3, wherein the method comprises the administration to said patient a therapeutically effective amount of a compound according to present invention or a pharmaceutically acceptable salt thereof Yet another aspect of the present invention is a method for treating, controlling, delaying or preventing in a mammalian patient in need thereof one or more conditions selected from the group consisting of an immunological, inflammatory, autoimmune, or allergic disorder or disease or a transplant rejection or a Graft-versus host disease, wherein the method comprises the administration to said patient a therapeutically effective amount of a compound according to present invention or a pharmaceutically acceptable salt thereof Yet another aspect of the present invention is a method for treating, controlling, delaying or preventing in a mammalian patient in need thereof a proliferative disease, especially cancer, wherein the method comprises the administration to said patient a therapeutically effective amount of a compound according to present invention or a pharmaceutically acceptable salt thereof.

In the context of these methods of the invention, diseases and disorders associated with JAK3 are as defined above.

As used herein, the term "treating" or "treatment" is intended to refer to all processes, wherein there may be a slowing, interrupting, arresting, or stopping of the progression of a disease, but does not necessarily indicate a total elimination of all symptoms.

All embodiments discussed above with respect to the pharmaceutical composition of the invention also apply to the above mentioned first or second medical uses or methods of the invention.

II. CHEMICAL DEFINITIONS

Various chemical definitions related to such compounds are provided as follows.

As used herein, the term "water soluble" means that the compound dissolves in water at least to the extent of 0.010 mole/liter or is classified as soluble according to literature precedence.

As used herein, the term "nitro" means —NO$_2$; the term "halo" designates —F, —Cl, —Br or —I; the term "mercapto" means —SH; the term "cyano" means —CN; the term "azido" means —N$_3$; the term "silyl" means —SiH$_3$, and the term "hydroxy" means —OH.

The term "alkyl," by itself or as part of another substituent, means, unless otherwise stated, a linear (i.e. unbranched) or branched carbon chain, which may be fully saturated, mono- or polyunsaturated. An unsaturated alkyl group is one having one or more double bonds or triple bonds. Saturated alkyl groups include those having one or more carbon-carbon double bonds (alkenyl) and those having one or more carbon-carbon triple bonds (alkenyl). The groups, —CH$_3$ (Me), —CH$_2$CH$_3$ (Et), —CH$_2$CH$_2$CH$_3$ (n-Pr), —CH(CH$_3$)$_2$ (iso-Pr), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), are all non-limiting examples of alkyl groups.

The term "heteroalkyl," by itself or in combination with another term, means, unless otherwise stated, a linear or branched chain having at least one carbon atom and at least one heteroatom selected from the group consisting of O, N, S, P, and Si. In certain embodiments, the heteroatoms are selected from the group consisting of O and N. The heteroatom(s) may be placed at any interior position of the heteroalkyl group or at the position at which the alkyl group is attached to the remainder of the molecule. Up to two heteroatoms may be consecutive. The following groups are all non-limiting examples of heteroalkyl groups: trifluoromethyl, —CH$_2$F, —CH$_2$Cl, —CH$_2$Br, —CH$_2$OH, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, CH$_2$CH$_2$OC(O)CH$_3$, —CH$_2$CH$_2$NHCO$_2$C(CH$_3$)$_3$, and —CH$_2$Si(CH$_3$)$_3$.

The terms "cycloalkyl" and "heterocyclyl," by themselves or in combination with other terms, means cyclic versions of "alkyl" and "heteroalkyl", respectively. Additionally, for heterocyclyl, a heteroatom can occupy the position at which the heterocycle is attached to the remainder of the molecule.

The term "aryl" means a polyunsaturated, aromatic, hydrocarbon substituent. Aryl groups can be monocyclic or polycyclic (e.g., 2 to 3 rings that are fused together or linked covalently). The term "heteroaryl" refers to an aryl group that contains one to four heteroatoms selected from N, O, and S. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

Various groups are described herein as substituted or unsubstituted (i.e., optionally substituted). Optionally substituted groups may include one or more substituents independently selected from: halogen, nitro, cyano, hydroxy, amino, mercapto, formyl, carboxy, oxo, carbamoyl, substituted or unsubstituted alkyl, substituted or unsubstituted heteroalkyl, alkoxy, alkylthio, alkylamino, (alkyl)$_2$amino, alkylsulfinyl, alkylsulfonyl, arylsulfonyl, substituted or unsubstituted cycloalkyl, substituted or unsubstituted heterocyclyl, substituted or unsubstituted aryl, and substituted or unsubstituted heteroaryl. In certain aspects the optional substituents may be further substituted with one or more substituents independently selected from: halogen, nitro, cyano, hydroxy, amino, mercapto, formyl, carboxy, carbamoyl, unsubstituted alkyl, unsubstituted heteroalkyl, alkoxy, alkylthio, alkylamino, (alkyl)$_2$amino, alkylsulfinyl, alkylsulfonyl, arylsulfonyl, unsubstituted cycloalkyl, unsubstituted heterocyclyl, unsubstituted aryl, or unsubstituted heteroaryl. Exemplary optional substituents include, but are not limited to: —OH, oxo (=O), —Cl, —F, Br, C$_{1-4}$alkyl, phenyl, benzyl, —NH$_2$, —NH(C$_{1-4}$alkyl), —N(C$_{1-4}$alkyl)$_2$, —NO$_2$, —S(C$_{1-4}$alkyl), —SO$_2$(C$_{1-4}$alkyl), —CO$_2$(C$_{1-4}$alkyl), and —O(C$_{1-4}$alkyl).

The term "alkoxy" means a group having the structure —OR', where R' is an optionally substituted alkyl or cycloalkyl group. The term "heteroalkoxy" similarly means a group having the structure —OR, where R is a heteroalkyl or heterocyclyl.

The term "amino" means a group having the structure —NR'R", where R' and R" are independently hydrogen or an optionally substituted alkyl, heteroalkyl, cycloalkyl, or heterocyclyl group. The term "amino" includes primary, secondary, and tertiary amines.

The term "oxo" as used herein means an oxygen that is double bonded to a carbon atom.

The term "alkylsulfonyl" as used herein means a moiety having the formula —S(O$_2$)—R', where R' is an alkyl group. R' may have a specified number of carbons (e.g. "C$_{1-4}$ alkylsulfonyl")

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydro fluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base such as methylamine, ethylamine, ethanolamine, lysine, ornithine and the like. Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable.

Additional examples of pharmaceutically acceptable salts and their methods of preparation and use are presented in Handbook of Pharmaceutical Salts: Properties, Selection and Use (2002), which is incorporated herein by reference.

An "isomer" of a first compound is a separate compound in which each molecule contains the same constituent atoms as the first compound, but where the configuration of those atoms in three dimensions differs. Unless otherwise specified, the compounds described herein are meant to encompass their isomers as well. A "stereoisomer" is an isomer in which the same atoms are bonded to the same other atoms, but where the configuration of those atoms in three dimensions differs. "Enantiomers" are stereoisomers that are mirror images of each other, like left and right hands. "Diastereomers" are stereoisomers that are not enantiomers.

It is contemplated that any embodiment discussed in this specification can be implemented with respect to any method or composition of the invention, and vice versa. Furthermore, compositions of the invention can be used to achieve methods of the invention.

III. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Preparation of 2-(hydroxymethyl)cyclododecanone

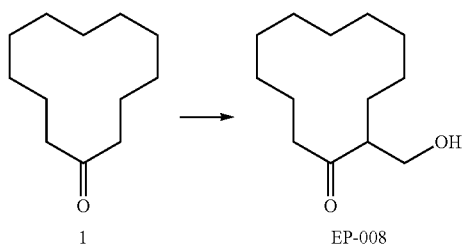 [SMILES: O=C1CCCCCCCCCCC1 ; O=C1CCCCCCCCCCC1CO]

Preparation of 2-(Hydroxymethyl)cyclododecanone (EP-008). To a solution of cyclododecanone (1) (5.0 g, 27.47 mmol, 1 equiv) and potassium carbonate (0.06 g, 0.41 mmol, 0.015 equiv) in acetonitrile (20 mL) and water (2 mL) was added formaldehyde (37% in water) (4.2 mL, 52.20 mmol, 1.9 equiv) at 40° C. dropwise. The reaction was stirred at 40° C. for 4 hours, then cooled to room temperature and extracted with diethyl ether (3×50 mL). The combined organic layers were dried over sodium sulfate, filtered, concentrated under reduced pressure. The crude product was purified on an AnaLogix system using a gradient of 0 to 30% ethyl acetate in heptanes to give the desired product as a clear oil, which slowly solidifies to a white solid (2.5 g, 43% yield).

Example 2

Preparation of 2-(hydroxymethyl)12-methylenecyclododecanone

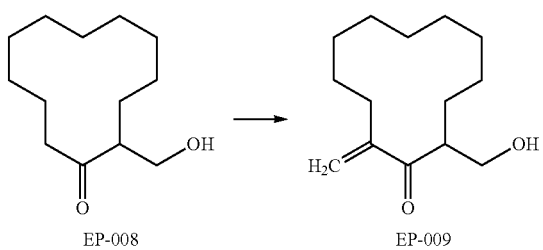 [SMILES: O=C1CCCCCCCCCCC1CO ; C=C1CCCCCCCCCC(CO)C1=O]

Preparation of 2-(Hydroxymethyl)-12-methylenecyclododecanone (EP-009). To a solution of compound EP-008 (0.20 g, 0.94 mmol, 1 equiv) in acetonitrile (4 mL) was added dibromomethane (1.6 mL, 22.6 mmol, 24 equiv) and diethylamine (4.7 mL, 45.2 mmol, 48 equiv). The reaction was placed in microwave at 80° C. for 5 hours. The reaction mixture was diluted with diethyl ether (50 mL), filtered, concentrated under reduced pressure. The crude product was purified on an AnaLogix system using a gradient of 0 to 20% ethyl acetate in heptanes to give the desired product as a clear wax (58 mg, 36% yield).

Example 3

Preparation of Sodium (3-methylene-2-oxocyclododecyl)methyl phosphate

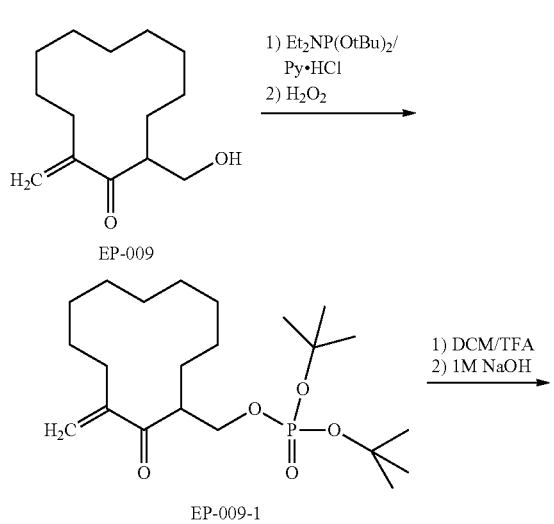

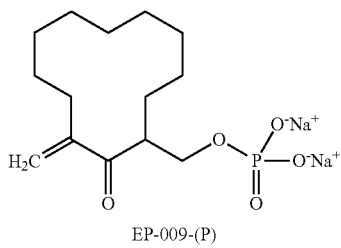

EP-009-(P)

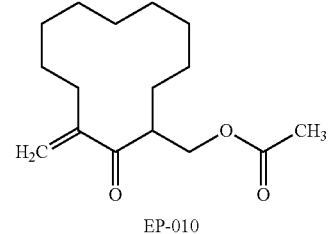

EP-010

Preparation of Sodium (3-methylene-2-oxocyclododecyl) methyl phosphate. Pyridine hydrochloride (1 g, 9 mmol, 2.0 equiv) and di-tert-butyl diethylphosphoramidite (2.5 mL, 9 mmol, 2.0 equiv) were added sequentially at 0° C. to a solution of EP-009 (1 g, 4.5 mmol, 1.0 equiv) in a 2 to 1 mixture of anhydrous tetrahydrofuran and DMF (60 mL). The reaction was warmed to room temperature and stirred for 2 hours, at which point LC/MS showed all the starting material had been consumed. A 35% aqueous hydrogen peroxide solution (1.3 mL, 13.5 mmol, 3.0 equiv) was added to the reaction and the mixture was stirred at room temperature for 12 hours. LC/MS showed the reaction was complete. The reaction was diluted with ethyl acetate and saturated brine. The layers were separated and the organic phase was washed with saturated brine (2×50 mL). The organic layer was dried over sodium sulfate, filtered, and concentrated under reduced pressure. The product was purified on an AnaLogix (SF25-60 g) column eluting with a gradient of 0 to 50% ethyl acetate in heptanes to give the desired product as a clear oil (1.6 g, 86% yield). Trifluoroacetic acid (3 mL) was added to a solution of compound EP-009-1 (1.6 g, 3.8 mmol, 1.0 equiv) in dichloromethane (200 mL). The reaction was stirred at room temperature for 3 hours, at which point TLC showed the reaction was completed. The solvent was evaporated under reduced pressure. The residue was dissolved in water (10 mL) and the mixture was adjusted to a pH 8 with 1M aqueous sodium hydroxide. The mixture was purified on an AnaLogix (SF25-100 g C18) column eluting with a gradient of 0 to 100% acetonitrile in water to give the desired product as a clear oil. The resulting oil was treated with ethyl acetate to obtain the product as an off white solid (1.3 g, 67% yield).

Example 4

Preparation of 3-Methylene-2-oxocyclododecyl)methyl acetate

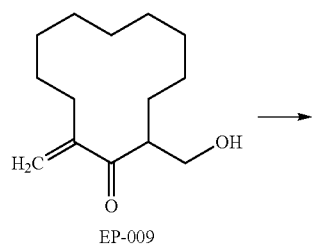

EP-009

Preparation of 3-Methylene-2-oxocyclododecyl)methyl acetate. To a solution of compound EP-009 (0.037 g, 0.165 mmol, 1 equiv) in dichloromethane (2 mL) was added triethylamine (0.116 mL, 0.825 mmol, 5 equiv) and 4-dimethylaminopyridine (0.010 g, 0.083 mmol, 0.5 equiv) at room temperature. Acetic anhydride (0.047 mL, 0.495 mmol, 3 equiv) was added and the reaction was stirred at room temperature for 2 hours. The reaction was concentrated under reduced pressure and the residue was purified on an AnaLogix system using a gradient of 0 to 30% ethyl acetate in heptanes to give the desired product as a white solid (40 mg, 91% yield).

Example 5

Characterization of Compounds

A. Results

Dose-Dependent Effect of (A) EP-008, (B) EP-009, (C) EP-009(P) and (D) EP-010 on IL-2/JAK3-Dependent Kit225 Cell Viability.

Kit225 cells were seeded in 96-well plates (3 wells/treatment) and treated with DMSO (0.1%) or ascending amounts of EP compound as indicated. MTS reagent was added and OD 490-650 nm determined at 72 h. Data represent mean OD normalized to DMSO treated control, while error bars represent the standard deviation (FIGS. 1A-1D).

Identification of EP009 as a Selective Inhibitor of JAK3 Kinase Activity.

Figures 2A, 2B, 2C, 2D, 2E, 2F:
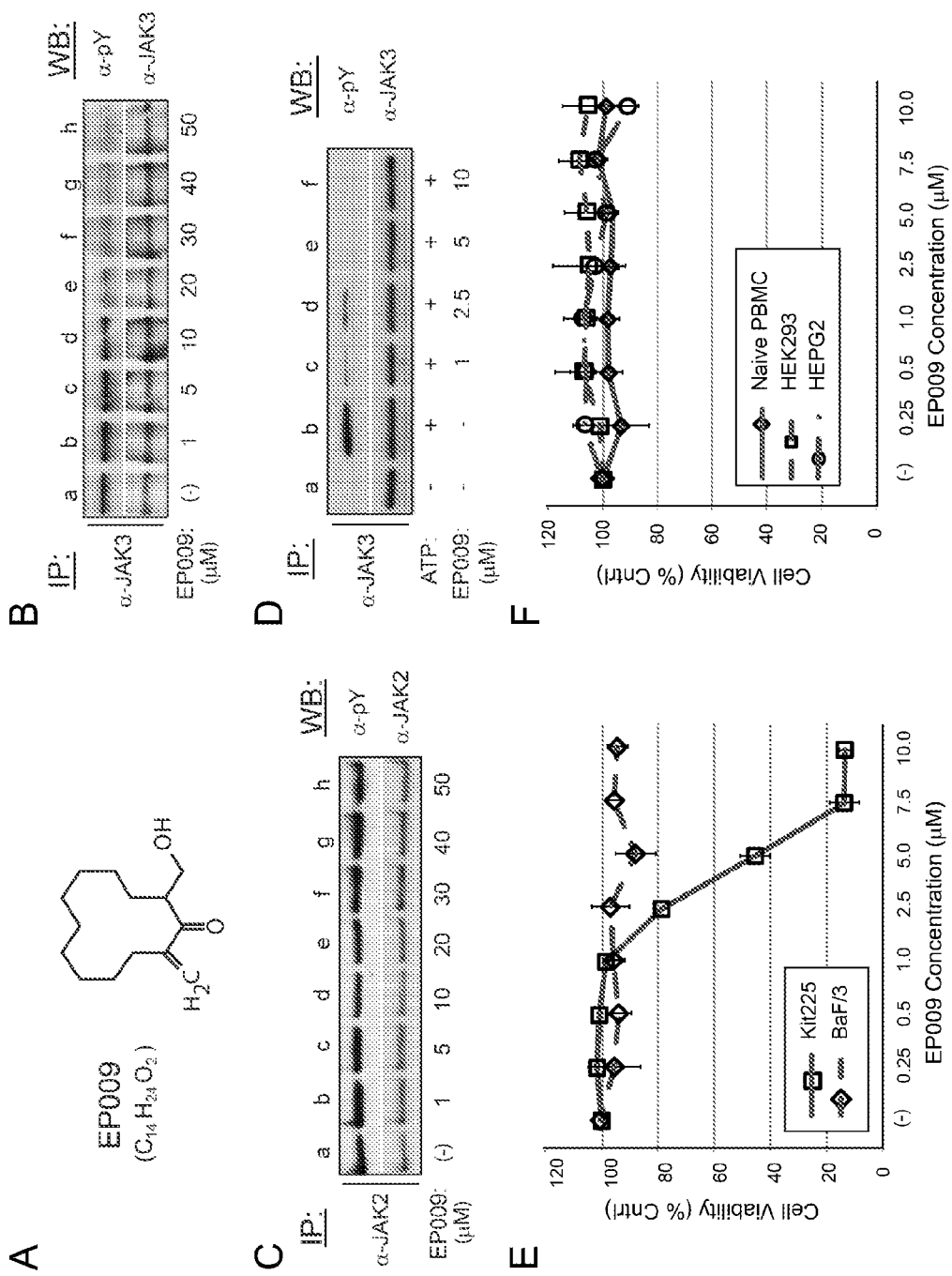
FIGS. 2A-2F. Selective inhibition of JAK3 by EP009 results in loss of JAK3-dependent tumor cell line viability with no detectable off-target effects in key cell types. (A) Chemical structure of EP009 (M.W. 224.34). (B) Kit225 or (C) BaF/3 cells cultured in the presence of IL-2 or IL-3, respectively, were treated with vehicle (PBS; lane a) or increasing amounts of EP009 (0-50 µM; lanes b-h) for 12 hours. Cells were then lysed, clarified, and immunoprecipitated (IP) with anti-JAK3 (α-JAK3) or anti-JAK2 (α-JAK2), and subjected to Western blot (WB) analysis with anti-phosphotyrosine (α-pY). Blots were stripped and reprobed with corresponding antibody to verify equivalent protein loading. (D) Immunopurified JAK3 was subjected to in vitro autokinase analysis after treatment with vehicle (DMSO; lanes a and b) or ascending concentrations of EP009 (0-10 µM; lanes c-f) for 1 hour at room temperature. The mixture was then incubated for 20 min at 30° C. in the absence (lane a) or presence (lanes b-f) of 1 µM unlabeled ATP before being separated by 7.5% SDS-PAGE and Western blotted with α-pY. The blot was stripped and reprobed with α-JAK3 to confirm equivalent loading. (E) Kit225 or BaF/3 cells were cultured with increasing amounts of EP009 (0-10 µM) for 72 hours and cell viability measured with the MTS tetrazolium salt assay. Values represent mean absorbance (OD490-OD650 nm) normalized to vehicle (PBS) treated control cells, while error bars represent the standard deviation (n=3). (F) HEK293, HEPG2, or naïve primary human PBMCs were cultured with increasing amounts of EP009 (0-10 µM) for 72 hours and cell viability measured with the MTS tetrazolium salt assay. Values represent mean absorbance (OD490-OD650 nm) normalized to vehicle (PBS) treated control cells, while error bars represent the standard deviation (n=3). Representative data from three independent experiments.
Figure 3:
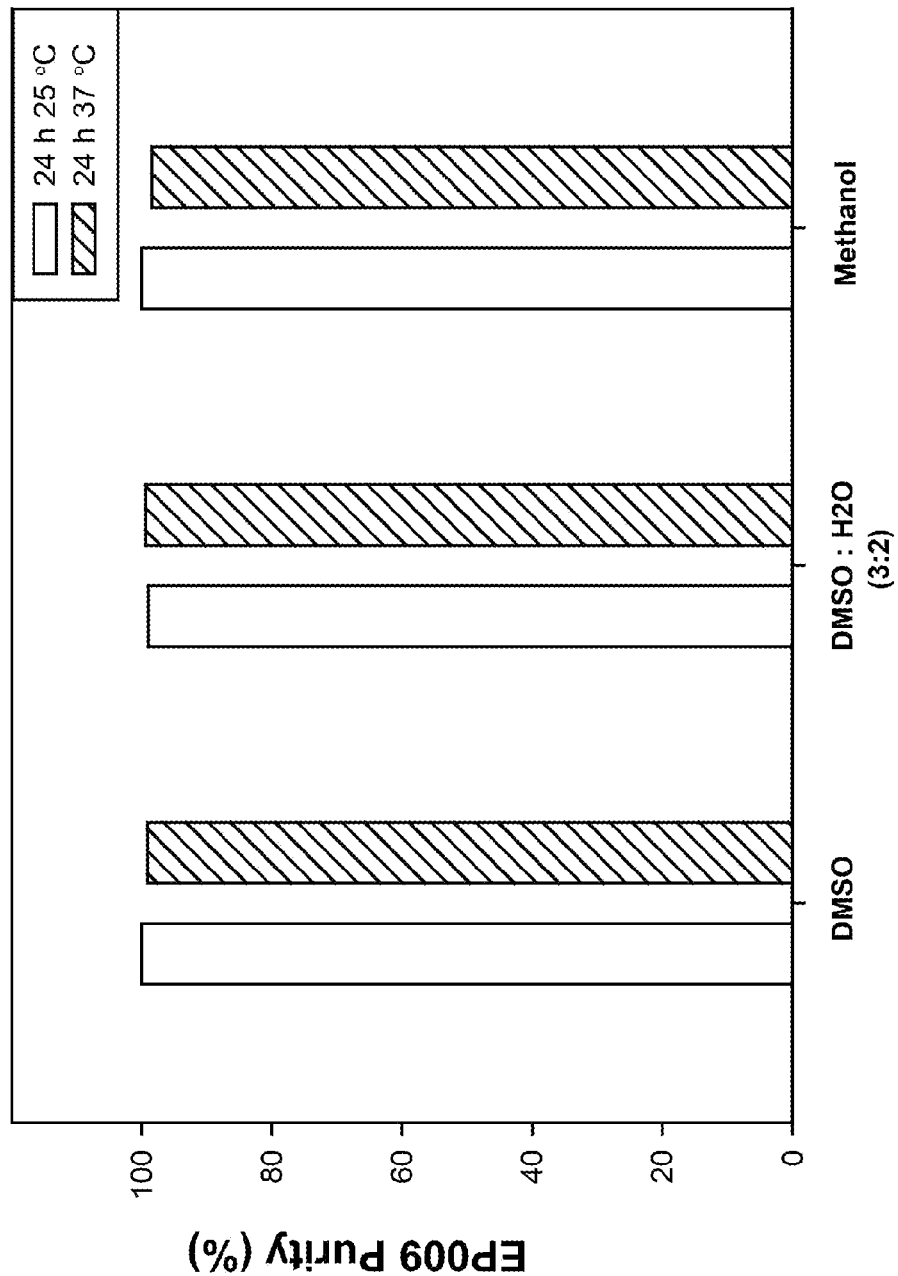
FIG. 3. EP009 is structurally stable under varying solvent and temperature conditions. EP009 was dissolved in DMSO, DMSO:H20 (3:2 ratio), or methanol, and incubated at 25° C. or 37° C. for 24 hours.

Achieving JAK3 selectivity remains a significant challenge in the development of new small molecules for the treatment of cancer and immune-derived diseases. As such, the inventors employed cell-based screening assays of small-molecule libraries based upon the chemical scaffold of the established JAK3 inhibitor NC1153 (Stepkowski et al., *J Immunol.* (2005), 175(7):4236-4246) EP009 (FIG. 2A) was selected as a lead compound due to improved intrinsic stability (>95% purity in various solvents at 37° C. for 24 hours; FIG. 3) and high-degree of JAK3 selectivity. To test JAK3 versus JAK2 specificity of EP009, the IL-2/JAK3-dependent Kit225, and IL-3/JAK2-dependent BaF/3 cell lines were used. Kit225 and BaF/3 cells growing in the presence of IL-2 or IL-3, respectively, were treated with ascending concentrations of EP009 for 12 hours and cellular JAK3 and JAK2 tyrosine phosphorylation levels detected by Western blot analysis (FIGS. 2B and 2C). Following densitometric analysis, EP009 was determined to dose-dependently reduce IL-2-mediated JAK3 tyrosine phosphorylation with a cellular 50% inhibitory concentration (IC50) between 10 and 20 μM (FIG. 2B). By contrast, EP009 had no detectable effect on IL-3-induced JAK2 tyrosine phosphorylation with concentrations up to 50 μM (FIG. 2C). To determine if EP009 mediated reduction in JAK3 tyrosine phosphorylation levels was due to inhibition of JAK3 autokinase activity, an in vitro kinase assay was performed. In the presence of 1 μM ATP, EP009 reduced the autokinase activity of immunopurified JAK3 with an IC50 value between 1 and 2.5 µM, as determined through densitometry analysis (FIG. 2D). In vitro IC50 values for kinase inhibitors are frequently lower than the cellular IC50 values due to potential cell permeability issues or external stimuli thresholds (i.e. cytokines) that must be overcome. To globally evaluate specificity, the inhibitory activity of EP009 was measured against a panel of protein kinases distributed throughout the kinome using the scanEDGE profiling service (KINOMEscan). At a concentration that abrogated JAK3 autokinase activity in vitro (10 µM), EP009 exhibited weak (<50%) inhibition against the kinases tested with the greatest inhibitory effect on Polo-like kinase 4 (PLK4) (47% inhibition) and Aurora kinase A (AURKA) (45% inhibition) (Table 1).

TABLE 1

In vitro enzyme inhibitory activity of EP009 on select protein kinases

| Accession Number | Entrez Gene Symbol | Kinase | Kinase Group | Kinase Activity (% of Control) |
|---|---|---|---|---|
| NP_005148.2 | ABL1 | ABL1(E255K)-phosphorylated | TK | 64 |
| NP_005148.2 | ABL1 | ABL1(T315I)-phosphorylated | TK | 100 |
| NP_005148.2 | ABL1 | ABL1-phosphorylated | TK | 100 |
| NP_004293.1 | ACVR1B | ACVR1B | TKL | 96 |
| NP_064632.2 | CABC1 | ADCK3 | Atypical | 98 |
| NP_005154.2 | AKT1 | AKT1 | AGC | 100 |
| NP_001617.1 | AKT2 | AKT2 | AGC | 100 |
| NP_004295.2 | ALK | ALK | TK | 100 |
| NP_003591.2 | AURKA | AURKA | Other | 55 |
| AAH00442.2 | AURKB | AURKB | Other | 99 |
| NP_001690.2 | AXL | AXL | TK | 96 |
| NP_001195.2 | BMPR2 | BMPR2 | TKL | 75 |
| NP_004324.2 | BRAF | BRAF | TKL | 72 |
| NP_004324.2 | BRAF | BRAF(V600E) | TKL | 76 |
| NP_000052.1 | BTK | BTK | TK | 91 |
| NP_055891.1 | CDC2L6 | CDK11 | CMGC | 100 |
| NP_001789.2 | CDK2 | CDK2 | CMGC | 98 |
| NP_001249.1 | CDK3 | CDK3 | CMGC | 100 |
| NP_001790.1 | CDK7 | CDK7 | CMGC | 99 |
| NP_001252.1 | CDK9 | CDK9 | CMGC | 90 |
| NP_001265.2 | CHEK1 | CHEK1 | CAMK | 100 |
| NP_005202.2 | CSF1R | CSF1R | TK | 94 |
| NP_620693.1 | CSNK1D | CSNK1D | CK1 | 100 |
| NP_001310.2 | CSNK1G2 | CSNK1G2 | CK1 | 100 |
| NP_004725.1 | DCAMKL1 | DCAMKL1 | CAMK | 100 |
| NP_004705.1 | DYRK1B | DYRK1B | CMGC | 100 |
| NP_005219.2 | EGFR | EGFR | TK | 100 |
| NP_005219.2 | EGFR | EGFR(L858R) | TK | 100 |
| NP_004422.2 | EPHA2 | EPHA2 | TK | 100 |
| NP_001005862.1 | ERBB2 | ERBB2 | TK | 100 |
| NP_001036064.1 | ERBB4 | ERBB4 | TK | 91 |
| NP_002737.2 | MAPK3 | ERK1 | CMGC | 100 |
| NP_722560.1 | PTK2 | FAK | TK | 69 |
| NP_075259.4 | FGFR2 | FGFR2 | TK | 100 |
| NP_000133.1 | FGFR3 | FGFR3 | TK | 100 |
| NP_004110.2 | FLT3 | FLT3 | TK | 99 |
| NP_002084.2 | GSK3B | GSK3B | CMGC | 100 |
| NP_000866.1 | IGF1R | IGF1R | TK | 100 |
| NP_001269.3 | CHUK | IKK-alpha | Other | 87 |
| NP_001547.1 | IKBKB | IKK-beta | Other | 73 |
| NP_000199.2 | INSR | INSR | TK | 100 |
| NP_002741.1 | MAPK8 | JNK1 | CMGC | 99 |
| NP_620707.1 | MAPK9 | JNK2 | CMGC | 100 |
| NP_002744.1 | MAPK10 | JNK3 | CMGC | 100 |
| NP_000213.1 | KIT | KIT | TK | 100 |
| NP_000213.1 | KIT | KIT(D816V) | TK | 100 |
| NP_000213.1 | KIT | KIT(V559D, T670I) | TK | 94 |
| NP_000446.1 | STK11 | LKB1 | CAMK | 100 |
| NP_005913.2 | MAP3K4 | MAP3K4 | STE | 87 |
| NP_116584.2 | MAPKAPK2 | MAPKAPK2 | CAMK | 100 |
| NP_002367.4 | MARK3 | MARK3 | CAMK | 100 |
| NP_002746.1 | MAP2K1 | MEK1 | STE | 71 |
| NP_109587.1 | MAP2K2 | MEK2 | STE | 84 |
| NP_000236.2 | MET | MET | TK | 89 |
| NP_001129025.1 | MKNK1 | MKNK1 | CAMK | 100 |
| NP_060042.2 | MKNK2 | MKNK2 | CAMK | 100 |
| NP_149132.2 | MAP3K9 | MLK1 | TKL | 100 |
| NP_620581.1 | MAPK14 | p38-alpha | CMGC | 100 |
| NP_002742.3 | MAPK11 | p38-beta | CMGC | 96 |
| NP_002567.3 | PAK1 | PAK1 | STE | 100 |
| AAA65442.1 | PAK2 | PAK2 | STE | 100 |
| NP_001014834.1 | PAK4 | PAK4 | STE | 100 |
| NP_006192.1 | CDK16 | PCTK1 | CMGC | 85 |
| NP_006197.1 | PDGFRA | PDGFRA | TK | 100 |
| NP_002600.1 | PDGFRB | PDGFRB | TK | 100 |

TABLE 1-continued

In vitro enzyme inhibitory activity of EP009 on select protein kinases

| Accession Number | Entrez Gene Symbol | Kinase | Kinase Group | Kinase Activity (% of Control) |
|---|---|---|---|---|
| NP_002604.1 | PDPK1 | PDPK1 | AGC | 100 |
| NP_002637.2 | PIK3C2B | PIK3C2B | Lipid | 70 |
| NP_006209.2 | PIK3CA | PIK3CA | Lipid | 76 |
| NP_002640.2 | PIK3CG | PIK3CG | Lipid | 75 |
| NP_002639.1 | PIM1 | PIM1 | CAMK | 100 |
| NP_006866.2 | PIM2 | PIM2 | CAMK | 100 |
| NP_001001852.1 | PIM3 | PIM3 | CAMK | 100 |
| NP_002721.1 | PRKACA | PKAC-alpha | AGC | 100 |
| NP_005021.2 | PLK1 | PLK1 | Other | 100 |
| NP_004064.2 | PLK3 | PLK3 | Other | 92 |
| NP_055079.2 | PLK4 | PLK4 | Other | 53 |
| NP_005391.1 | PRKCE | PRKCE | AGC | 100 |
| NP_002871.1 | RAF1 | RAF1 | TKL | 97 |
| NP_065681.1 | RET | RET | TK | 100 |
| NP_060813.2 | RIOK2 | RIOK2 | Atypical | 69 |
| NP_004841.2 | ROCK2 | ROCK2 | AGC | 99 |
| NP_112214.1 | NUAK2 | SNARK | CAMK | 82 |
| NP_005408.1 | SRC | SRC | TK | 100 |
| NP_055185.2 | SRPK3 | SRPK3 | CMGC | 100 |
| NP_004603.1 | TGFBR1 | TGFBR1 | TKL | 100 |
| NP_000450.2 | TEK | TIE2 | TK | 90 |
| NP_001012331.1 | NTRK1 | TRKA | TK | 65 |
| NP_114417.1 | TSSK1B | TSSK1B | CAMK | 98 |
| NP_055498.3 | ULK2 | ULK2 | Other | 58 |
| NP_002244.1 | KDR | VEGFR2 | TK | 100 |
| NP_775846.2 | STK32C | YANK3 | AGC | 98 |
| NP_997402.1 | ZAP70 | ZAP70 | TK | 99 |

EP009 Selectively Reduces Viability of JAK3-Dependent Cells with No Off-Target Effects in Key Cell Types.

Figure 4A:
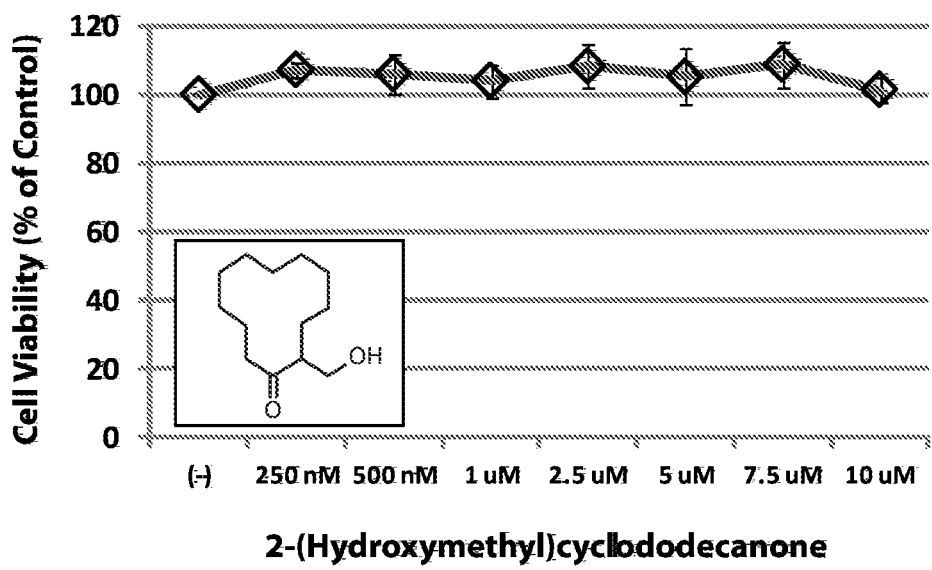
FIG. 4. EP009 structure-activity relationship studies. Kit225 cells were cultured with increasing amounts of (A) 2-(Hydroxymethyl)cyclododecanone or (B) 3-(Methylene-2-oxododecyl)methyl acetate (0-10 µM) for 72 hours and cell viability measured with the MTS tetrazolium salt assay. Values represent mean absorbance (OD490-OD650 nm) normalized to vehicle (DMSO) treated control cells, while error bars represent the standard deviation (n=3).
Figure 4B:
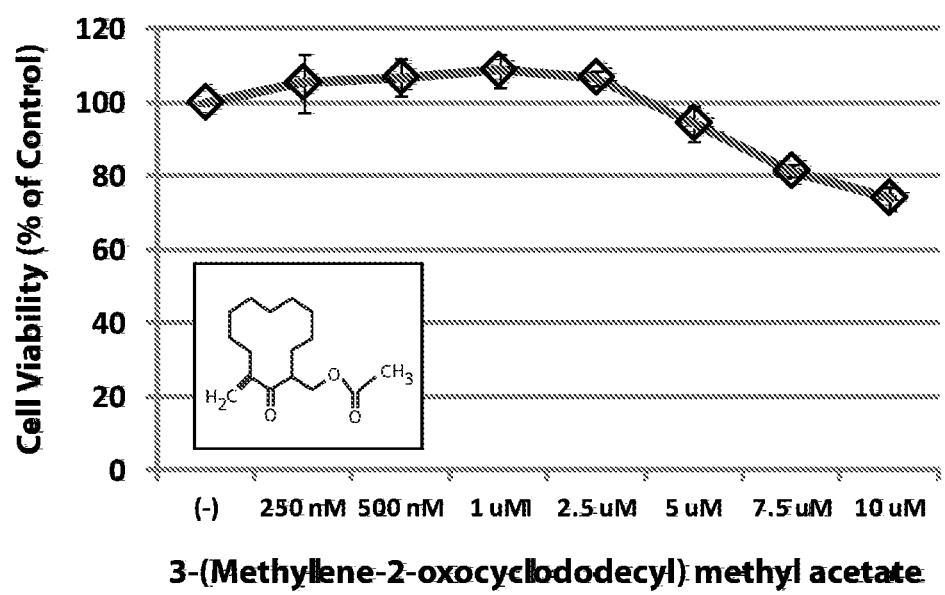
Figure 5A:
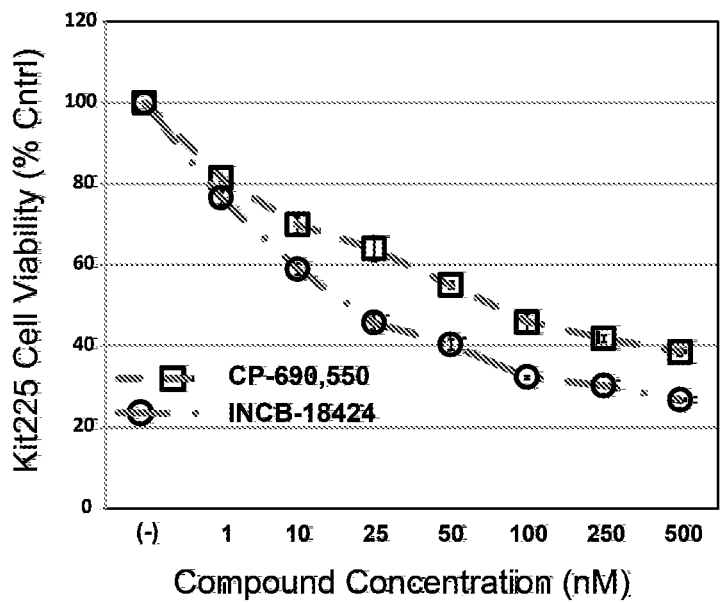
FIGS. 5A-5B. Effect of JAK inhibitors CP-690,550 and INCB-18424 on Kit225 and BaF/3 cell viability. (A) Kit225 and (B) BaF/3 cells were cultured with increasing amounts of CP-690,550 or NCB-18424 (0-500 nM) for 72 hours and cell viability measured with the MTS tetrazolium salt assay. Values represent mean absorbance (OD490-OD650 nm) normalized to vehicle (DMSO) treated control cells, while error bars represent the standard deviation (n=3).
Figure 5B:
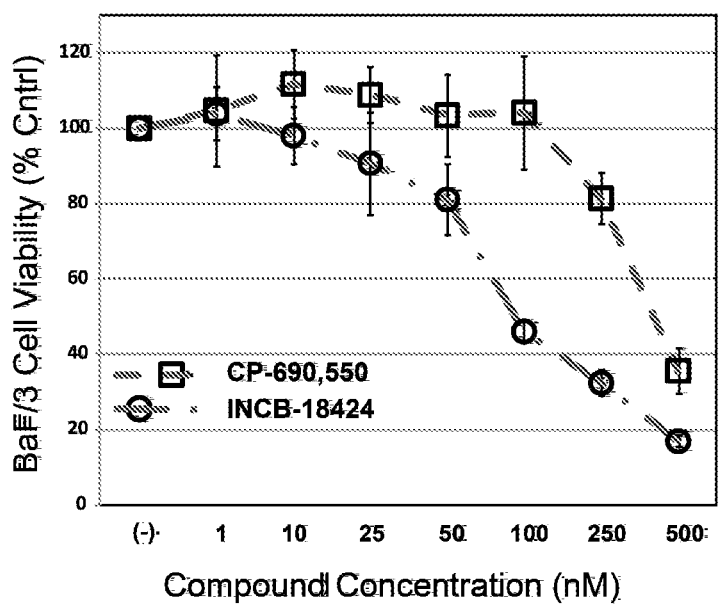

The effects of graded EP009 concentrations on the viability of IL-2/JAK3 dependent Kit225 and IL-3/JAK2-dependent BaF/3 cells were assessed. Treatment of Kit225 cells resulted in a 55% reduction in cell viability at 5.0 μM EP009, while 7.5-10 μM EP009 resulted in maximal loss of Kit225 cell viability at 72 hours (FIG. 2E). In contrast, identical concentrations of EP009 had no effect on BaF/3 cell viability at 72 hours (FIG. 2E). The sensitivity differentials between the enzyme (FIG. 2B) and cell viability assays presumably arise from the differences in durations of EP009 treatments that are required by the respective assays due to their kinetically distinct readouts. Structure-activity relationship studies revealed that deletion of the C12 methylene or substitution at the C2 hydroxymethyl groups of the cyclododecanone ring significantly reduced the cellular potency of EP009 (FIGS. 4A-4B). Under the same experimental conditions the JAK inhibitors tofacitinib (CP-690,550) and ruxolitinib (INCB-18424) reduced both Kit225 and BaF/3 cell viability at 72 hours (FIGS. 5A-5B).

The effects of EP009 on cell types that survival has not been directly linked to JAK3 was examined, including the human kidney cell line HEK293, human liver cell line HEPG2, and normal human naïve PBMCs. HEK293 and HEPG2 cells are commonly used in drug toxicity studies to assess possible effects on renal and hepatic systems, respectively, (Hettiarachchi et al. PloS one. (2010), 5(5):e10514) and normal naïve human PBMCs express little JAK3 protein (Ross et al., J Biol Chem. 2007). Indeed, treatment of these cells with EP009 for 72 hours resulted in no detectable loss of cell viability at concentrations that resulted in complete loss of JAK3-dependent cell viability (FIG. 2F).

EP009 Inhibits Constitutively-Active JAK3/STAT3 Signaling and Reduces CD30 Cell Surface Expression in ALCL Cells.

Figures 6A, 6B, 6C, 6D:
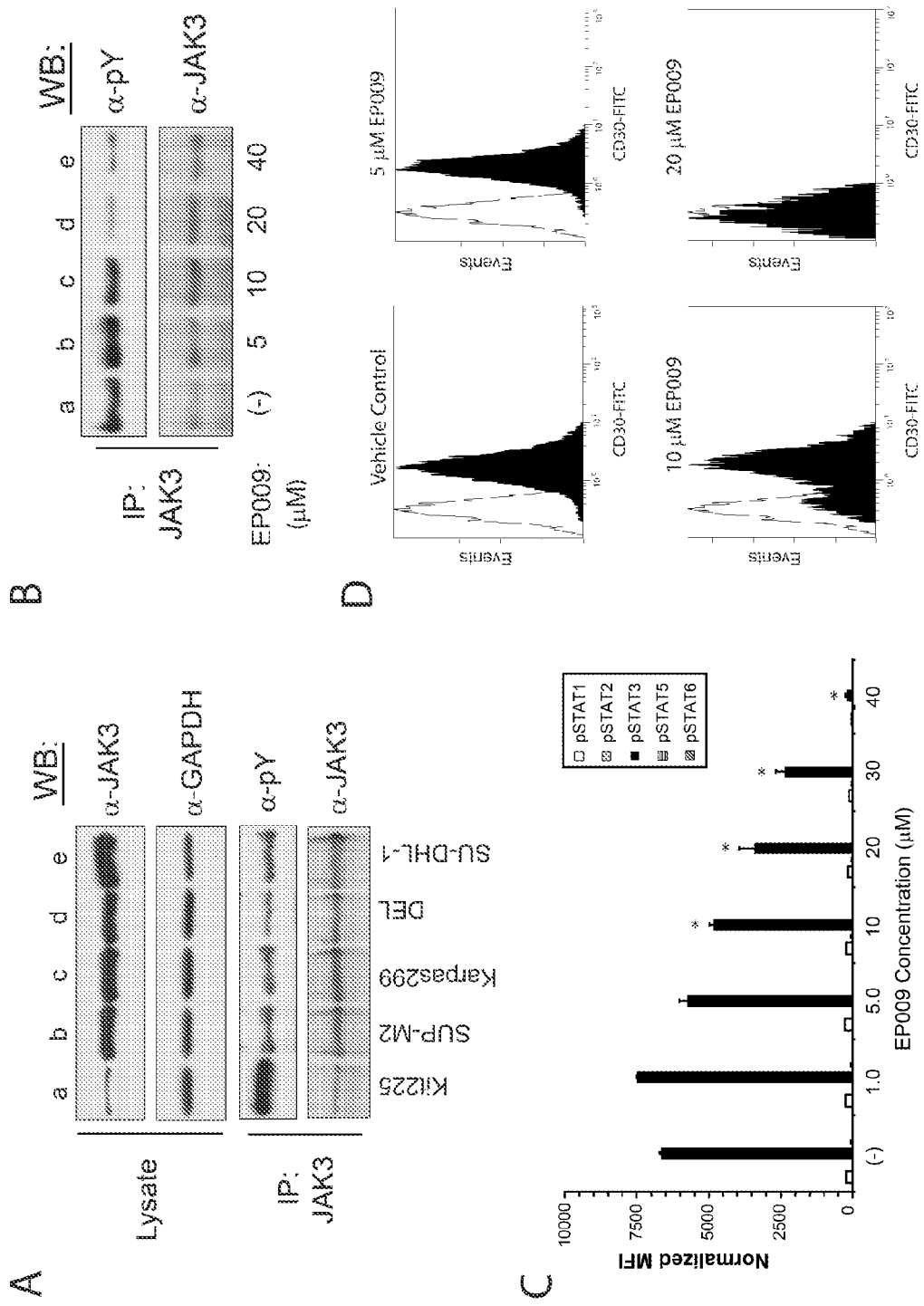
FIGS. 6A-6B. EP009 treatment disrupts constitutive JAK3/STAT3 pathway activation and down-regulates CD30 cell surface expression in human ALCL cells. (A) Kit225 (lane a), SUP-M2 (lane b), Karpas299 (lane c), DEL (lane d) and SU-DHL-1 (lane e) total cell lysates were separated by 7.5% SDS-PAGE (upper panel) or were immunoprecipitated (IP) with JAK3 antibodies (lower panel) and separated on 7.5% SDS-PAGE, and then subjected to Western blot (WB) analysis with the indicated antibodies. (B) SU-DHL-1 cells were treated with vehicle (PBS; lane a) or increasing amounts of EP009 (0-40 µM; lanes b-e) for 12 hours. Cells were then lysed, clarified, and immunoprecipitated (IP) with anti-JAK3 (α-JAK3), and subjected to Western blot (WB) analysis with anti-phosphotyrosine (α-pY). Blots were stripped and reprobed with α-JAK3 to verify equivalent protein loading. (C) SU-DHL-1 cells were treated with vehicle (PBS) or increasing amounts of EP009 (0-40 µM) for 12 hours. Cells were then lysed, clarified, and subjected to Luminex multiplex analysis to detect tyrosine phosphorylated STAT1 (pSTAT1), STAT2 (pSTAT2), STAT3 (pSTAT3), STAT5A/B (pSTAT5), and STAT6 (pSTAT6). Values represent pSTAT mean fluorescence intensity (MFI) normalized to corresponding GAPDH MFI, while error bars represent the standard deviation (n=2). Statistical significance was determined using Student's t-test. (*, p<0.05). (D) SU-DHL-1 cells were treated with vehicle (PBS) or increasing amounts of EP009 for 24 hours. Cells were then analyzed by flow cytometry for CD30 expression. Representative data from three independent experiments.

The ability of EP009 to inhibit JAK3 activity in lymphoid tumor cell lines that display constitutively-active JAK3 protein were assessed. In previous studies of NPM-ALK-positive ALCL, inhibition of constitutively-active JAK3 was shown to down-regulate STAT3 phosphorylation and induce apoptosis (Lai et al., Hum Pathol. (2005), 36(9):939-944; Amin et al. Oncogene. (2003), 22(35):5399-5407; Qiu et al. Blood. (2006), 108(7):2407-2415; Dien et al. The American journal of pathology. (2009), 175(2):825-834). Western blot analysis revealed that JAK3 protein expression is 5 fold greater in ALCL cell lines SUP-M2, Karpas299, DEL and SU-DHL-1 compared to Kit225 cells (FIG. 6A, upper panel). Furthermore, JAK3 was found constitutively active in the ALCL cell lines tested, which is in agreement with previously reported findings (FIG. 6A, lower panel). Therefore, the effect of EP009 treatment on constitutively-active JAK3 in ALCL cells was determined. Treatment of SU-DHL-1 cells with EP009 for 12 hours resulted in a dose-dependent reduction in JAK3 tyrosine phosphorylation levels with a 70% decrease observed at 20 μM EP009 compared to vehicle treated control cells (FIG. 6B). To determine whether the effect of EP009 on JAK3 phosphorylation in ALCL cells correlates with inhibition of downstream effector STAT activation, SU-DHL-1 cells were exposed to increasing amounts of EP009 for 12 hours and analyzed tyrosine phosphorylation levels of STAT1, STAT2, STAT3, STAT5 and STAT6 using multiplex analyses. EP009 treatment resulted in a dose-dependent inhibition of phospho-STAT3 levels compared to control treated cells (FIG. 6C). Constitutive tyrosine phosphorylation of STAT1, STAT2, STAT5 or STAT6 was not detected, which supports earlier reports that STAT3 is the major effector STAT in SU-DHL-1 cells (Chiarle et al. Nature medicine. (2005), 11(6):623-29).

The inventors have shown that JAK3 inhibition in YT and Kit225 lymphoid tumor cells repressed CD30 gene expression (Nagy et al. *FEBS letters*. (2010), 584(8):1515-20). To evaluate whether CD30 expression was affected by suppression of JAK3 in SU-DHL-1 cells, CD30 surface expression was monitored by flow cytometry analysis at different dosages of EP009 treatment for 24 hours. As shown in FIG. 6D, dose-dependent CD30 down-regulation was observed in EP009 treated cells, when compared with the vehicle treated cells. The down-regulation of CD30 expression in SU-DHL-1 cells correlated to the level of JAK3 and STAT3 inhibition post EP009 treatment (FIGS. 6B and 6C). Indeed, activated STAT3 has been shown to enhance CD30 transcription in ALCL cells (Chiarle et al. *Nature medicine*. (2008), 14(6): 676-80).

EP009 Reduces ALCL Cell Viability Through Induction of Caspase 3 Mediated Apoptosis.

Figure 7A:
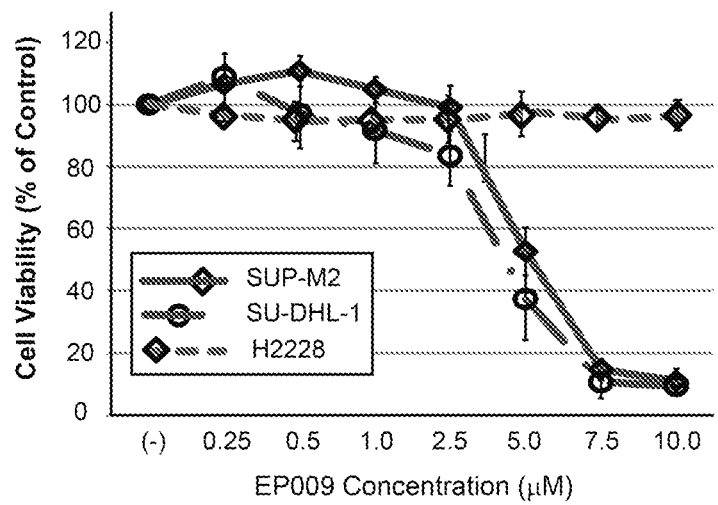
FIGS. 7A-7C. EP009 reduces ALCL cell viability through induction of caspase 3 mediated apoptosis. (A) SUP-M2, SU-DHL-1 or H2228 cells were cultured with increasing amounts of EP009 (0-10 µM) for 72 hours and cell viability measured with the MTS tetrazolium salt assay. Values represent mean absorbance (OD490-OD650 nm) normalized to vehicle (PBS) treated control cells, while error bars represent the standard deviation (n=3). (B) SU-DHL-1 cells were treated with vehicle (PBS) or increasing amounts of EP009 (0-50 µM) for 24 hours. Cells were then lysed, clarified, and subjected to Luminex multiplex analysis to detect activated caspase 3 and (C) cleaved PARP. Values represent MFI normalized to corresponding GAPDH MFI, while error bars represent the standard deviation (n=2). Representative data from three independent experiments are shown. Statistical significance was determined using Student's t-test. (*, p<0.05).
Figure 7B:
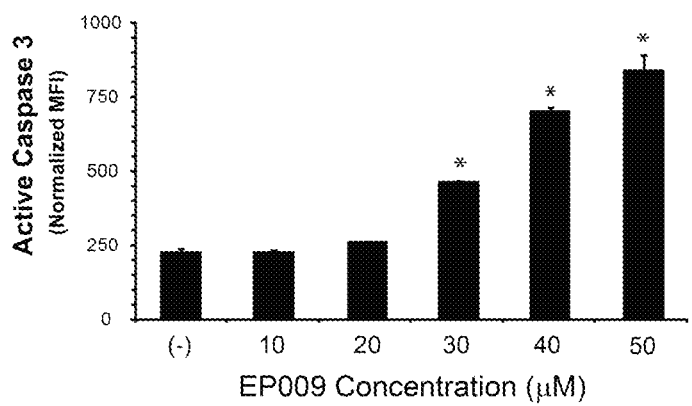
Figure 7C:
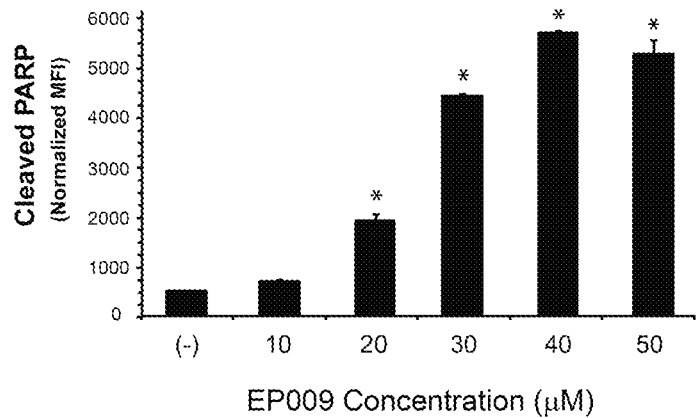

To assess the functional outcome of JAK3 inhibition in ALCL cells, the effect of EP009 treatment on SU-DHL-1 and SUP-M2 cell viability were monitored. EP009 treatment led to a concentration-dependent reduction in viability of SU-DHL-1 and SUP-M2 cells with an IC50 of 5 μM at 72 hours (FIG. 7A). In contrast, treatment with EP009 had no effect on cell viability of the EML4-ALK-positive, but JAK3-negative, non-small cell lung cancer cell line H2228, further supporting the specificity of EP009 toward JAK3 and its functional role in ALCL (FIG. 7A). To gain additional insight into the molecular mechanism by which EP009 reduces cell viability in ALCL cells, the inventors assessed the activation status of caspase 3 and downstream cleavage of poly(ADP-ribose) polymerase (PARP), both of which are hallmarks of apoptosis (Decker and Kovarik. *Oncogene*. (2000), 19(21):2628-37). Treatment of SU-DHL-1 cells with EP009 for 24 hours increased both caspase-3 activation and PARP cleavage in a dose-dependent manner (FIGS. 7B and 7C).

EP009 Mediated JAK3 Inhibition Results in Activation of ERK1/2 and JNK1/2 MAPKs and Inhibition of p70 S6 Kinase in ALCL Cells.

Figures 8A, 8B, 8C, 8D, 8E, 8F:
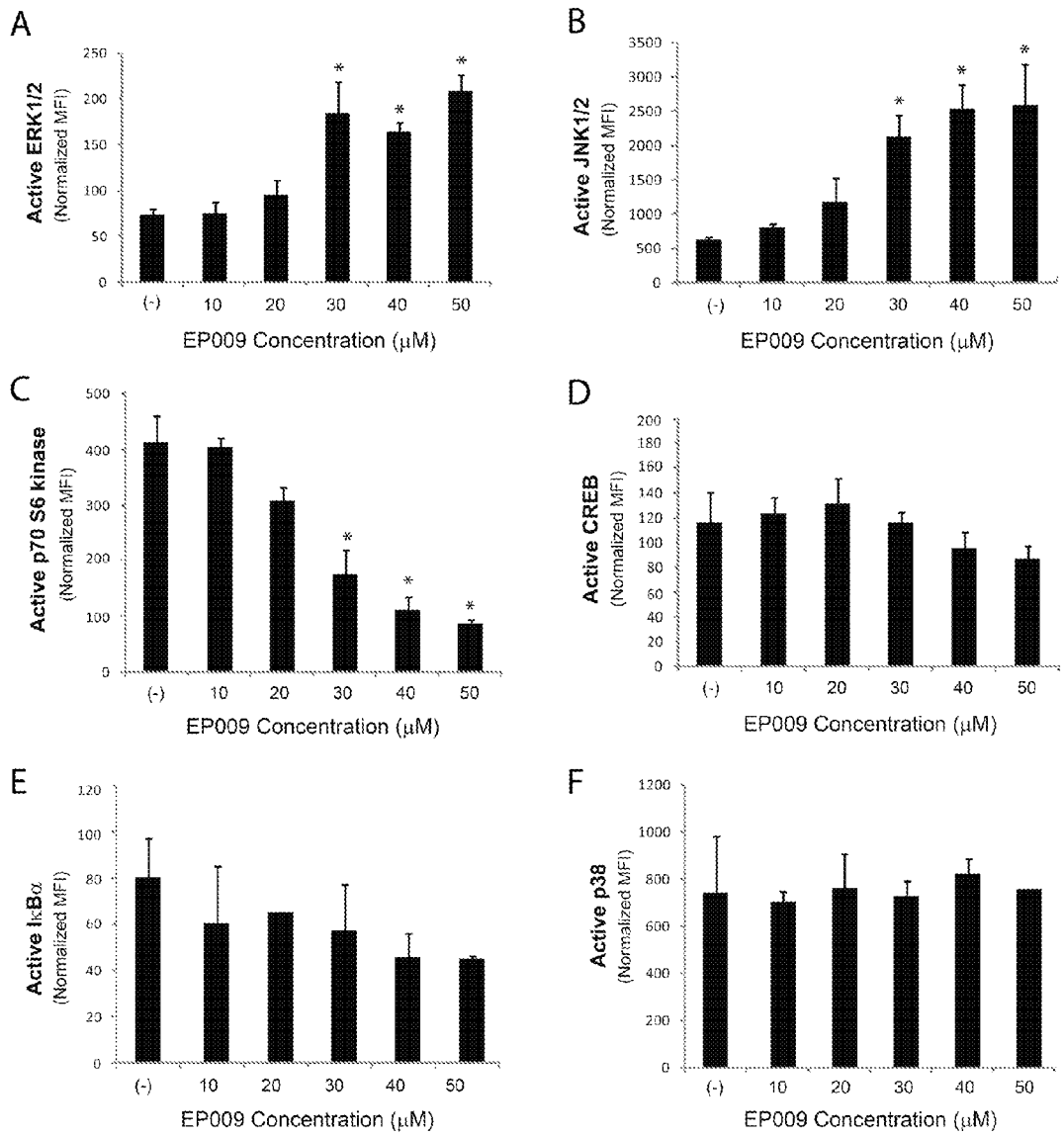
FIGS. 8A-8F. Effect of EP009 on ALCL cells is mediated through selective activation of ERK1/2 and JNK1/2 stress signaling pathways, and inhibition of p70 S6 kinase growth signaling pathways. SU-DHL-1 cells were treated with vehicle (PBS) or increasing amounts of EP009 (0-50 µM) for 24 hours. Cells were then lysed, clarified, and subjected to Luminex multiplex analysis to detect phosphorylated (A) ERK1/2, (B) JNK1/2, (C) p70 S6 kinase, (D) IκBα, (E) CREB, and (F) p38. Values represent mean fluorescence intensity (MFI) normalized to corresponding GAPDH MFI, while error bars represent the standard deviation (n=2). Representative data from two independent experiments are shown. Statistical significance was determined using Student's t-test. (*, p<0.05).

To further elucidate the molecular mechanisms whereby EP009 induces cell death, key members of survival and stress-responsive cell signaling pathways were analyzed in SU-DHL-1 cells upon treatment with or without EP009 for 24 hours. Results from multiplex analyses revealed that EP009 induced phosphorylation and activation of ERK1/2 and JNK1/2 mitogen activated protein (MAP) kinases in a dose-dependent manner (FIGS. 8A and 8B). Conversely, constitutive phosphorylation of p70 S6 kinase was decreased in a dose-dependent manner upon treatment with EP009 (FIG. 8C). No statistically significant change in p38 MAP kinase, CREB or IκBα phosphorylation status was detected (FIGS. 8D, 8E and 8F) however p38 MAP kinase was found to be constitutively active in these cells, but no further activation beyond basal levels was noted (FIG. 8F).

EP009 Reduces Tumor Burden in Xenograft Model of Human Lymphoma.

Figure 9A:
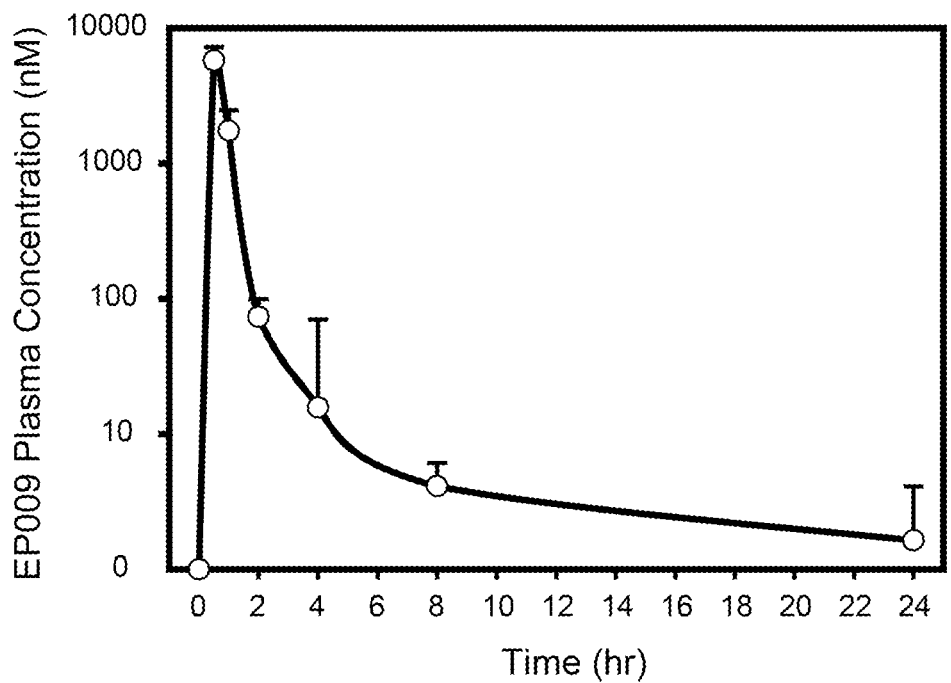
FIGS. 9A-9B Pharmacokinetics and efficacy of EP009 in vivo. (A) Sprague Dawley rats were administered EP009 by oral gavage (200 mg/kg) and pharmacokinetics measured by analysis of plasma concentrations at indicated time points. Values represent mean concentrations, while error bars represent the standard deviation (n=5). (B) Therapeutic study of EP009 in SU-DHL-1 model in SCID/NOD mice. Treatments with oral EP009 given at 100 (n=8, square) and 200 mg/kg (n=8, triangle) inhibited the SU-DHL-1 lymphoma growth significantly as seen by tumor sized compared to the control group (n=8, circle) * p<0.05; ** p<0.01.
Figure 9B:
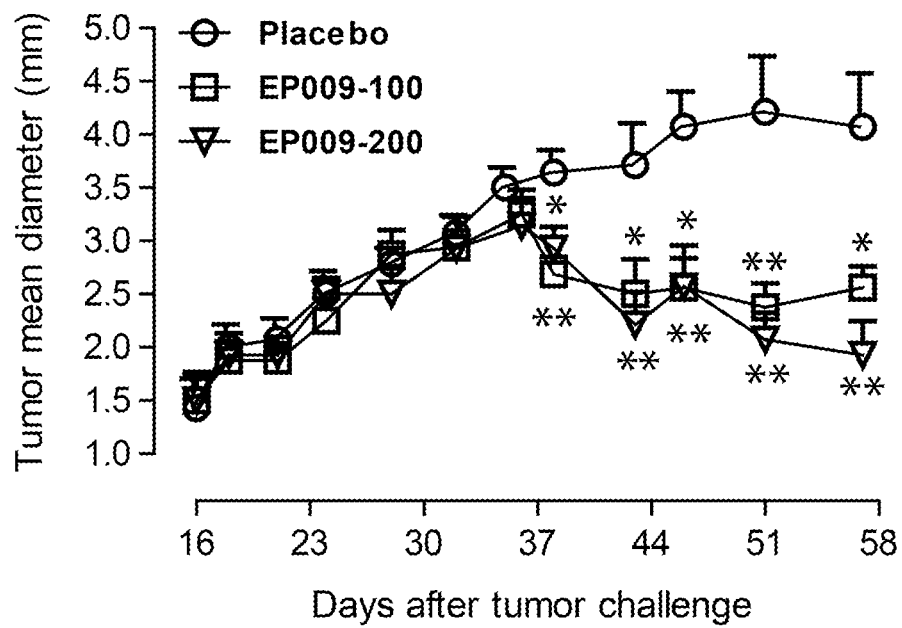

To determine oral bioavailability of EP009, the plasma concentration in rats (n=5) was determined after single oral dose of 200 mg/kg over a period of 24 hours. Sprague Dawley rats were used instead of mice to avoid inter-animal variability by utilizing the same animal for the duration of the experiment. EP009 reached peak plasma concentration (Cmax) of 2.00 μg/ml (5.74 μM), an area under the concentration-time curve (AUC-t) of 2.11 μg/ml h (6.10 μM. h), and a half-life (t1/2) of 1 hour after EP009 oral administration (FIG. 9B). Plasma levels of EP009 eight hours after dosing declined to the limit of detection. These data indicate that tumor xenografts would be exposed to plasma levels consistent with the cytotoxic levels of EP009 observed in cell-based studies (FIG. 2E and FIG. 7A). Therefore, to test the anti-tumor activity of EP009, a xenograft mouse model using SU-DHL-1 cells was employed. SU-DHL-1 tumors in the control group grew steadily until termination of the experiment (FIG. 9B). However, mice (N=8 per group) treated with oral EP009 given at 100 mg/kg and 200 mg/kg showed significant tumor growth inhibition of 37.5% (p<0.05) and 51% (p<0.01), respectively (FIG. 9A). The anti-tumor response initiated 37 days post tumor challenge and was maintained for the remainder of the protocol. No statistical difference was observed between 100 and 200 mg/kg, suggesting that anti-tumor responses induced by EP009 at these doses may have reached a plateau curve. No significant body weight changes following oral administration of EP009 at 100 and 200 mg/kg were observed (data not shown).

Stability analysis of the NC1153 dihydrochloride salt (structure shown in FIG. 10A) using NMR and HPLC indicates the compound decomposes from cleavage of a single dimethylamino group (Elimination Product). (FIG. 10B) Although soluble in water, NC1153 decomposes at an observed rate of 10% and 33% in 24 hr at 25° C. and 37° C., respectively (FIGS. 10A-10B).

Detection and Stability Analysis of EP-009.

Figure 12:
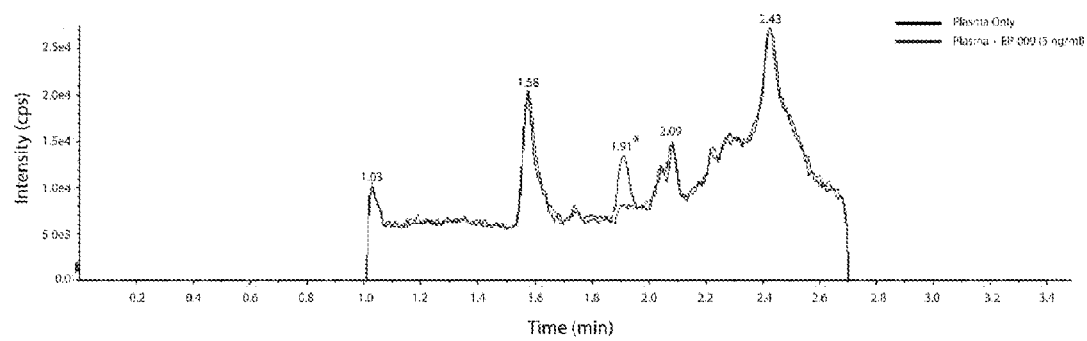
FIG. 12 illustrates LC-MS/MS detection of EP-009 (5 ng/ml) in mouse plasma at a retention time of 1.91 min.
Figure 13:
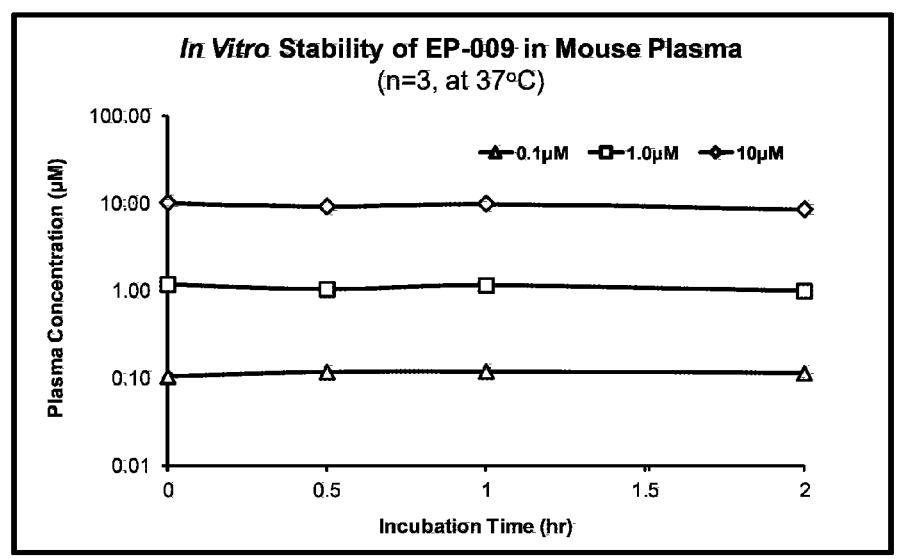
FIG. 13 illustrates EP-009 is stable and readily detected in mouse plasma at the indicated concentrations and incubation time points.

Stability analysis of EP-009 using NMR and HPLC indicates the compound is stabile under various solubility conditions in 24 hr at 25° C. and 37° C. FIG. 11 illustrates the dose-dependent effect of (FIG. 11A) freshly prepared EP-009 (P) and (FIG. 11B) EP-009(P) stored in aqueous conditions for 48 hr at room temperature on IL-2/JAK3-dependent Kit225 cell viability. FIG. 12 illustrates LC-MS/MS detection of EP-009 (5 ng/ml) in mouse plasma at a retention time of 1.91 min. FIG. 13 illustrates EP-009 is stable and readily detected in mouse plasma at the indicated concentrations and incubation time points.

LD50 of EP009 IV in Mice.

Mice were dosed using EP009 (-P) by intravenous tail vein injection. 25 mice were divided into groups of 5 and given doses of 2.0 mg (group B), 4.0 mg (group C), 6.0 mg (group D), and 8.0 mg (group E) of EP009, along with a placebo control (group A), in a volume of 100 pt. This corresponded to doses of 100, 200, 300, 400 mg/kg, and 0 mg/kg (control). Dosing began at 3:15 p.m., and began with the highest dose group, followed by 6, 4, 2, and the control group. Dosing took around 15 minutes.

By the time the last mouse was dosed, the entire high dose group (Group E) was dead. Two mice in the D group were also dead at the time dosing was completed. One mouse in the D group also exhibited a slight activity decrease, but was back to normal in 48 hours. Mouse 3 and 5 in Group D had necrotic tails. This is most likely due to an imperfect injection that leaked slightly from the tail vein. After the initial deaths, no other deaths were observed. Thus, it was conclude that dose limiting safety in vivo was between 200-300 mg/kg of EP009 given IV as bolus.

B. Methods and Materials

Reagents and Cell Lines.

EP009, the designation for 2-(hydroxymethyl)-12-methylene-cyclododecanone, was synthesized by Adesis Inc (New Castle, Del.). For all cell-based and in vivo experiments with EP009, the water-soluble disodium phosphate form (sodium (3-methylene-2-oxocyclododecyl)methyl phosphate) with 98.5% purity was used. INCB-18424 and CP-690,550 were purchased from Selleck Chemicals and LC Laboratories, respectively. The human YT, DEL, Karpas299, SU-DHL-1, SUP-M2, HEK293, HEPG2, and NCI-H2228 (ATCC: CRL-5935) cell lines were maintained as previously described.24 The human IL-2-dependent T-cell line Kit225 was maintained in medium containing 10 IU/ml human recombinant IL-2 (NCI Preclinical Repository). The murine IL-3-dependent pro-B-cell line Ba/F3 was maintained in the above medium containing 1 ng/ml murine IL-3 (PeproTech). Human peripheral blood mononuclear cells (PBMCs) were obtained from healthy donors and purified by isocentrifugation as previously described.24

Cell Culture and Treatment.

The IL-2 dependent human chronic lymphocytic leukemia (CLL) derived T-cell line Kit225, the IL-3 murine pro-B cell line BaF3, and the anaplastic large cell lymphoma (ALCL) cell lines DEL, SU-DHL1, Karpas 299 and SUP-M2 (kindly provided by Dr. G Inghirami, Torino, Italy) were maintained in RPMI-1640 medium containing 10% fetal bovine serum, 2 mM L-glutamine and penicillin-streptomycin (50 IU/ml and 50 mg/ml, respectively), at 37° C. and 5% CO2. Kit225 media was supplemented with 10 IU/ml human recombinant IL-2 (NCI Preclinical Repository). BaF3 media was supplemented with 1 ng/ml murine IL-3 (R&D Systems). Freshly explanted normal human peripheral blood mononuclear cells (PBMCs) were purified by isocentrifugation (Ficoll®). Cells were treated with indicated concentration of compound or vehicle control (DMSO or PBS) for the times indicated.

Viability (MTS) Assay:

Cell viability was assessed with 3-(4,5-dimethylthiazol-2-yl)-5-(3-carboxymethoxyphenyl)-2-(4-sulfophenyl)-2H-tetrazolium salt (MTS) reagent (Promega) in triplicates according to the manufacturer's instructions. Three independent experiments were performed. The error bars represent standard deviation.

Solubilization of Membrane Proteins, Immunoprecipitation, and Western Blot Analysis.

Cell pellets were solubilized in Triton lysis buffer (10 mM Tris-HCl (pH 7.6), 5 mM EDTA (pH 8.0), 50 mM NaCl, 30 mM $Na_4P_2O_7$, 50 mM NaF, 1 mM $Na_3VO_4$, 1% Triton X-100) containing 1 mM phenylmethylsulfonyl fluoride, 5 µg/ml aprotinin, 2 µg/ml leupeptin, 1 µg/ml pepstatin A and clarified by centrifugation (16,000×g, 10 min, 4° C.). For immunoprecipitation reactions, supernatants were rotated with 2 µl of indicated antibody for 2 h at 4° C. The immune complexes were captured by incubation for 30 minutes at 4° C. with protein A-Sepharose beads (Rockland Immunochemicals). The beads were then washed 3 times with cold lysis buffer and eluted by boiling in 1×SDS sample buffer (50 mM Tris-HCl (pH 6.8), 100 mM dithiothreitol, 2% SDS, 0.02% bromophenol blue, 10% glycerol, pH 6.8). Samples were resolved by 7.5% SDS-PAGE, transferred to PVDF membrane (Immobilon P, Millipore). For phospho-Stat5 assays, approximately 10 mg of total cell lysate was dissociated in SDS-sample buffer and separated on 10% SDS-PAGE under reducing conditions. Western blot analysis was performed with the indicated primary antibodies either overnight (α-pY Stat5) or for 1 h (for other primary antibodies) at room temperature. Western blots were developed with horseradish peroxidase-conjugated secondary antibodies using enhanced chemiluminescence (ECL) and X-Ray film. When reblotting, PVDF membranes were cleaned in stripping buffer (100 mM β-mercaptoethanol, 2% SDS, and 62.5 mM Tris-HCl (pH 6.7)) at 55° C. for 30 min, blocked and then probed with a second primary antibody.

Kinase Assays:

Analysis of EP-009 mediated inhibition of the protein kinase panel was performed according to the Upstate Biotechnology Cell Signaling Solutions and Kinase Profiler. All EP-009 inhibitory kinase reactions were initiated in the presence of 10 µM ATP and normalized to vehicle. JAK3 autokinase assays were performed using immunopurified JAK3 from YT cells resuspended in kinase buffer (25 mM Tris-HCl [pH 7.5], 5 mM β-glycerophosphate, 10 mM $MgCl_2$, 2 mM dithiothreitol, 0.1 mM $Na_3VO_4$) in the absence or presence of the indicated concentration of EP009. Reaction mixtures were incubated at room temperature for one hour followed by addition of 1 µM ATP and incubation at 30° C. for 20 min before termination by adding SDS sample buffer. Samples were resolved by 7.5% SDS-PAGE and tyrosine phosphorylation levels of JAK3 were assessed by Western blotting with α-pY and α-JAK3 antibodies.

Flow Cytometry.

Cells were treated in the absence or presence of the indicated concentrations of EP009 for 24 hours, and stained with FITC-labeled mouse anti-human CD30 (Millipore). Stained cells were analyzed by flow cytometry (Cytomics FC500, Beckman Coulter) and quantitated with CXP analysis software version 2.2 (Beckman Coulter) as previously described.24

Multiplex Analysis.

Target proteins were analyzed using xMAP technology on the Luminex 200 platform coupled with xPONENT 3.1 software (Luminex) according to the manufacturer's suggested protocol. The MILLIPLEX MAP 8-plex Multi-Pathway Signaling Phosphoprotein kit (Millipore) was used to detect phosphorylated ERK1/2 (Thr185/Tyr187), STAT3 (Ser727), JNK1/2 (Thr183/Tyr185), p70 S6 kinase (Thr412), IκBα (Ser32), STAT5A/B (Tyr694/699), CREB (Ser133), and p38 (Thr180/Tyr182). The MILLIPLEX MAP 5-plex STAT Phosphoprotein kit (Millipore) was used to detect phosphorylated STAT1 (Tyr701), STAT2 (Tyr690), STAT3 (Tyr705), STAT5A/B (Tyr694/699), and STAT6 (Tyr641). The MILLIPLEX MAP Human Apoptosis 3-plex kit (Millipore) was used to detect cleaved PARP, cleaved Caspase 3, and total GAPDH for protein normalization.

EP009 Pharmacokinetics.

EP009 (200 mg/kg) was administered orally to Sprague Dawley rats (Texas Animal Specialties) of ~200 g weight (n=5) after an overnight fast. Blood (~200 µl) was drawn at 0.5, 1, 2, 4, 8 and 24 hours after dosing and plasma was collected and snap-frozen in liquid nitrogen. EP009 plasma concentrations were determined by a liquid chromatography tandem mass spectrometry (LC-MS/MS) system. This system included a HPLC (Shimadzu Scientific Corporation) with an ACE C18 column (50×2.1 mm, 5 um) and an API-4000 (triple-quadruple) mass spectrometer (ABSciex, Inc) with an electrospray ionization source. A positive multiple reaction monitoring (MRM) scan was applied. The mobile phase A and B used in this study were 0.1% formic acid in 5 mM ammonium acetate and 0.1% formic acid in 100% acetonitrile. Plasma samples (50 µL) were mixed with 50 µL of blank plasma and 300 µL of internal standard solution (Verapamil, 20 ng/mL in 100% acetonitrile). After vortexing for 1 min and centrifuging for 5 min at 16,000×g, 300 µL supernatants were analyzed by LC-MS/MS. The limit of quantitation was 1 ng/mL of EP009 in plasma and the calibration range was from 1 to 2000 ng/mL.

Mouse Model.

Severe combined immunodeficient/nonobese diabetic (SCID/NOD) mice were purchased from Charles River (Milan, Italy). The SU-DHL-1 model, 28 which was established by subcutaneous injection of 1×107 SU-DHL-1 cells in the left flank of SCID/NOD mice, served as the xenograft human lymphoma model. Tumor masses were measured with caliper in two perpendicular diameters in a blind fashion to determine the longest diameter. Progressively growing masses >1 mm in diameter were regarded as tumors. Mice were divided into three groups (n=8/group) and treatments initiated when tumors were established and measurable (day 16 after tumor challenge). Control mice received oral gavage of saline (placebo), while treated mice received EP009 orally (100 or 200 mg/kg) three times per week for six weeks. The study was terminated when tumors began to show signs of ulcerations and measurements became inaccurate (day 58). All animal were maintained in the animal facility of the Molecular Biotechnology Center, University of Turin and treated in accordance with the European guidelines.

Statistical Analyses.

Student's t-tests were employed for pair-wise comparison of treatments, using SigmaStat3.1 (SyStat, Aspire Software International) software. p-values <0.05 were considered statistically significant.

The invention claimed is:

1. A prodrug of a JAK kinase inhibitor having a formula of Formula Ib:

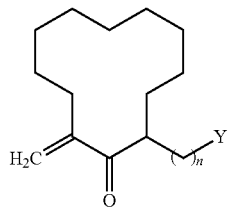

Formula Ib wherein n is 0, 1, 2, 3, 4, 5, or 6; and Y is a promoiety that results in alcohol derivative of the parent compound upon removal.

2. The prodrug of claim 1, wherein Y is phosphate, phosphonate, phosphate salt, sulfate, or sulfate salt.

3. A method of inhibiting JAK kinase activity in a patient comprising administering an effective amount of the prodrug of claim 1 to a patient in need thereof.

4. The method of claim 3, wherein the patient has or is at risk of developing an immunological, inflammatory, autoimmune, allergic, or hyperproliferative disorder.

5. The method of claim 3, wherein the patient is a cancer patient.

6. The method of claim 5, wherein the cancer is a hematopoietic cancer.

* * * * *